US012715937B2

(12) United States Patent
Nielsen et al.

(10) Patent No.: US 12,715,937 B2
(45) Date of Patent: Aug. 25, 2026

(54) BI-SPECIFIC FUSION PROTEINS

(71) Applicant: Silver Creek Pharmaceuticals, Inc., San Francisco, CA (US)

(72) Inventors: Ulrik Bjerl Nielsen, Quincy, MA (US); Thomas Wickham, Groton, MA (US); Birgit Schoeberl, Cambridge, MA (US); Brian Harms, Roslindale, MA (US); Bryan Linggi, Richland, WA (US); Matthew Onsum, Jamaica Plain, MA (US); Byron DeLaBarre, Cambridge, MA (US)

(73) Assignee: Silver Creek Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 18/311,306

(22) Filed: May 3, 2023

(65) Prior Publication Data

US 2023/0322951 A1 Oct. 12, 2023

Related U.S. Application Data

(60) Continuation of application No. 17/078,978, filed on Oct. 23, 2020, now Pat. No. 11,673,970, which is a (Continued)

(51) Int. Cl.

| | |
|---|---|
| ***C07K 16/46*** | (2006.01) |
| ***A61K 38/00*** | (2006.01) |

(Continued)

(52) U.S. Cl.

CPC .............. *C07K 16/46* (2013.01); *A61K 45/06* (2013.01); *A61K 47/66* (2017.08); (Continued)

(58) Field of Classification Search

CPC ...... C07K 16/46; C07K 14/47; C07K 14/475; C07K 14/485; C07K 14/65; C07K 16/44; (Continued)

(56) References Cited

U.S. PATENT DOCUMENTS

| | | | |
|---|---|---|---|
| 5,273,966 | A | 12/1993 | Sknottner-Lundin et al. |
| 5,632,986 | A | 5/1997 | Tait et al. |

(Continued)

FOREIGN PATENT DOCUMENTS

| | | |
|---|---|---|
| AU | 2008-200706 | 3/2008 |
| AU | 2015-204540 | 8/2016 |

(Continued)

OTHER PUBLICATIONS

Rivadeneyra-Espinoza et al., Cell-penetrating anti-native DNA antibodies trigger apoptosis through both the neglect and programmed pathways. J Autoimmun. Feb. 2006;26(1):52-6. doi: 10.1016/j.jaut.2005.10.008. Epub Dec. 20, 2005. PMID: 16368224. (Year: 2005).*

(Continued)

*Primary Examiner* — Randall L Beane

(74) *Attorney, Agent, or Firm* — Greenberg Traurig, LLP; Natalie Salem; David J. Dykeman

(57) ABSTRACT

Bi-specific fusion proteins with therapeutic uses are provided, as well as pharmaceutical compositions comprising such fusion proteins, and methods for using such fusion proteins to repair damaged tissue. The bi-specific fusion proteins generally comprise: (a) a targeting polypeptide domain that binds to an ischemia-associated molecule; and (b) an activator domain that that detectably modulates the activity of a cellular network.

2 Claims, 1 Drawing Sheet

Specification includes a Sequence Listing.

Leader polypeptide (optional) — Targeting polypeptide domain — Short Connector Polypeptide (optional) — HSA polypeptide — Short Connector Polypeptide (optional) — Activator domain — polyhistidine comprising polypeptide (optional)

Related U.S. Application Data division of application No. 15/957,252, filed on Apr. 19, 2018, now Pat. No. 10,858,450, which is a division of application No. 14/187,728, filed on Feb. 24, 2014, now Pat. No. 9,982,060, which is a division of application No. 13/112,907, filed on May 20, 2011, now Pat. No. 8,691,771.

(60) Provisional application No. 61/347,040, filed on May 21, 2010.

(51) Int. Cl.

| | |
|---|---|
| ***A61K 45/06*** | (2006.01) |
| ***A61K 47/66*** | (2017.01) |
| ***A61K 47/68*** | (2017.01) |
| ***B82Y 5/00*** | (2011.01) |
| ***C07K 14/47*** | (2006.01) |
| ***C07K 14/475*** | (2006.01) |
| ***C07K 14/485*** | (2006.01) |
| ***C07K 14/65*** | (2006.01) |
| ***C07K 16/44*** | (2006.01) |
| ***C12N 15/62*** | (2006.01) |

(52) U.S. Cl.

CPC ...... *A61K 47/6811* (2017.08); *A61K 47/6891* (2017.08); *B82Y 5/00* (2013.01); *C07K 14/47* (2013.01); *C07K 14/475* (2013.01); *C07K 14/485* (2013.01); *C07K 14/65* (2013.01); *C07K 16/44* (2013.01); *C12N 15/62* (2013.01); *A61K 38/00* (2013.01); *C07K 2317/31* (2013.01); *C07K 2317/76* (2013.01); *C07K 2319/00* (2013.01); *C07K 2319/80* (2013.01)

(58) Field of Classification Search

CPC ............ C07K 2317/31; C07K 2317/76; C07K 2319/00; C07K 2319/80; A61K 45/06; A61K 47/66; A61K 47/6811; A61K 47/6891; A61K 38/00; B82Y 5/00; C12N 15/62; A61P 1/16; A61P 1/18; A61P 7/00; A61P 9/00; A61P 11/00; A61P 13/12; A61P 17/00; A61P 19/02; A61P 19/08; A61P 25/00; A61P 43/00

See application file for complete search history.

(56) References Cited

U.S. PATENT DOCUMENTS 5,679,771 A 10/1997 Ballard et al.
6,387,663 B1* 5/2002 Hall .................. A61K 38/1866 424/9.4
6,541,610 B1 4/2003 Smith
6,566,098 B1 5/2003 Chan et al.
7,226,907 B1 6/2007 Zhou
7,396,918 B2 7/2008 Glass et al.
7,459,541 B2 12/2008 Hall et al.
7,521,211 B2 4/2009 Glass
7,531,318 B2 5/2009 Srivastava et al.
7,576,186 B2 8/2009 Lum et al.
7,612,164 B2 11/2009 Zhou
7,786,074 B2 8/2010 Gourdie et al.
7,837,999 B2 11/2010 Glass et al.
8,067,357 B2 11/2011 Reutelingsperger et al.
8,158,581 B2 4/2012 Glass et al.
8,445,434 B2 5/2013 Glass et al.
8,691,771 B2* 4/2014 Nielsen .................. C07K 14/65 514/21.3
8,748,380 B2 6/2014 Plumridge et al.
9,238,080 B2* 1/2016 Nielsen .................. C07K 16/44
9,718,892 B2* 8/2017 Nielsen .................. A61K 47/66
9,982,060 B2* 5/2018 Nielsen .................... B82Y 5/00
10,040,840 B2* 8/2018 Antipov .................. A61P 43/00
10,407,512 B2* 9/2019 Nielsen ..................... A61P 7/00
10,633,425 B2 4/2020 Antipov et al.
10,858,450 B2* 12/2020 Nielsen .................. A61P 13/12
10,988,547 B2* 4/2021 Nielsen .................. C07K 16/44
11,155,593 B2 10/2021 Antipov et al.
11,673,970 B2* 6/2023 Nielsen .................. A61P 13/12 424/134.1
11,814,443 B2* 11/2023 Nielsen .................. A61P 17/00
11,879,002 B2 1/2024 Antipov et al.
12,122,819 B2 10/2024 Antipov et al.
2003/0153490 A1* 8/2003 Tchelingerian ......... A61P 43/00 530/359
2004/0213738 A1 10/2004 Croll-Kalish et al.
2005/0043236 A1 2/2005 Daly et al.
2005/0164926 A1 7/2005 Wun
2005/0287151 A1 12/2005 Glass
2006/0018897 A1 1/2006 Lee et al.
2006/0223753 A1* 10/2006 Glass .................... C07K 14/65 514/6.9
2006/0228299 A1* 10/2006 Thorpe ............. A61K 47/6898 424/1.49
2006/0275254 A1 12/2006 Kim et al.
2007/0048282 A1 3/2007 Rosen et al.
2007/0054851 A1* 3/2007 Lin .......................... A61P 3/10 514/4.8
2007/0110733 A1 5/2007 Lum
2007/0172811 A1 7/2007 Srivastava et al.
2007/0224119 A1 9/2007 McTavish
2008/0039341 A1* 2/2008 Schellenberger ...... C07K 14/61 506/13
2008/0050370 A1 2/2008 Glaser et al.
2008/0069823 A1* 3/2008 Allison .................. A61K 47/55 514/17.7
2008/0071063 A1* 3/2008 Allan ..................... A61P 29/00 530/387.1
2008/0241118 A1 10/2008 LeBowitz
2009/0068181 A1 3/2009 Lee et al.
2009/0093407 A1 4/2009 Hall et al.
2009/0126920 A1 5/2009 Demuth et al.
2009/0214507 A1 8/2009 Srivastava et al.
2010/0055115 A1 3/2010 Lum et al.
2010/0197890 A1 8/2010 McTavish
2010/0291080 A1 11/2010 Lee et al.
2011/0045007 A1 2/2011 Schuurman et al.
2011/0059076 A1 3/2011 McDonagh et al.
2011/0274658 A1 11/2011 Silver et al.
2011/0286976 A1* 11/2011 Nielsen .................. A61P 25/00 536/23.4
2011/0293579 A1 12/2011 Nielsen et al.
2012/0177652 A1 7/2012 Nielsen et al.
2012/0244163 A1 9/2012 Schoeberl et al.
2014/0178380 A1 6/2014 Nielsen et al.
2014/0315817 A1 10/2014 Schmidt et al.
2016/0168269 A1 6/2016 Nielsen et al.
2017/0335015 A1 11/2017 Nielsen et al.
2018/0237540 A1 8/2018 Nielsen et al.
2020/0048368 A1 2/2020 Nielsen et al.

FOREIGN PATENT DOCUMENTS

| | | |
|---|---|---|
| CA | 2286264 | 10/1998 |
| CA | 2768621 | 1/2011 |
| CA | 2902744 | 10/2014 |
| EP | 854884 | 7/1998 |
| EP | 1141015 | 10/2001 |
| EP | 1436316 | 7/2004 |
| EP | 2 275 446 | 1/2011 |
| EP | 2900255 | 8/2014 |
| WO | WO 1992/008495 | 5/1992 |
| WO | WO 1994/028133 | 12/1994 |
| WO | WO 1995/032003 | 11/1995 |
| WO | WO 1996/033698 | 10/1996 |
| WO | WO 2000/002587 | 1/2000 |
| WO | WO 2002/017951 | 3/2002 |
| WO | WO 2005/117973 | 12/2005 |
| WO | WO 2006/003488 | 1/2006 |
| WO | WO 2006/004910 | 1/2006 |
| WO | WO 2006/076525 | 7/2006 |

(56) References Cited

FOREIGN PATENT DOCUMENTS

| | | |
|---|---|---|
| WO | WO 2006/079120 | 7/2006 |
| WO | WO 2006/091209 | 8/2006 |
| WO | WO 2006/128125 | 11/2006 |
| WO | WO 2007/021494 | 2/2007 |
| WO | WO 2007/044887 | 4/2007 |
| WO | WO 2007/095338 | 8/2007 |
| WO | WO 2008/063424 | 5/2008 |
| WO | WO 2008/089567 | 7/2008 |
| WO | WO 2008/091209 | 8/2008 |
| WO | WO 2008/096158 | 8/2008 |
| WO | WO 2008/151005 | 12/2008 |
| WO | WO 2008/155134 | 12/2008 |
| WO | WO 2009/030720 | 3/2009 |
| WO | WO 2009/126920 | 10/2009 |
| WO | WO 2010/059315 | 5/2010 |
| WO | WO 2011/011071 | 1/2011 |
| WO | WO 2011/146902 | 11/2011 |
| WO | WO 2012/078153 | 6/2012 |
| WO | WO 2013/075066 | 11/2012 |
| WO | WO 2013/086785 | 6/2013 |

OTHER PUBLICATIONS

Park et al., Crystal structure of single-domain VL of an anti-DNA binding antibody 3D8 scFv and its active site revealed by complex structures of a small molecule and metals. Proteins. Jun. 2008;71(4):2091-6. doi: 10.1002/prot.22011. PMID: 18338383 (Year: 2008).*

Forsberg et al., Separation and characterization of modified variants of recombinant human insulin-like growth factor I derived from a fusion protein secreted from *Escherichia coli*. Biochem J. Oct. 15, 1990;271(2):357-63. doi: 10.1042/bj2710357. PMID: 2173560; PMCID: PMC1149562 (Year: 1990).*

Gadgil et al., Affinity purification of DNA-binding proteins. J Biochem Biophys Methods. Oct. 30, 2001;49(1-3):607-24. doi: 10.1016/s0165-022x(01)00223-8. PMID: 11694305 (Year: 2001).*

Adderson, E., et al., "Molecular analysis of polyreactive monoclonal antibodies from rheumatic carditis: human anti-N-acetylglucosamine/anti-myosin antibody V region genes," J Immunol., 161(4):2020-2031, (Aug. 15, 1998).

Andrades, et al., "Engineering, expression, and renaturation of a collagen-targeted human bFGF fusion protein," Growth Factors, 18:261-275, (Aug. 1999).

Askari, et al., "Effect of stromal-cell-derived factor 1 on stem-cell homing and tissue regeneration in ischaemic cardiomyopathy," Mechanisms of Disease, 362: 697-703, (Aug. 30, 2003).

Bai et al., "Tracking long-term survival of intramyocardially delivered human adipose tissue-derived stem cells using bioluminescence imaging," Molecular Imaging and Biology, 13 pages (Aug. 21, 2010).

Barbas, S., et al., "Human autoantibody recognition of DNA," Proc Natl Acad Sci U S A, 92(7):2529-2533, (Mar. 28, 1995).

Bauwens, C., et al., "Geometric control of cardiomyogenic induction in human pluripotent stem cells", Tissue Eng., Part A, (Apr. 25, 2011).

Bayne, Marvin et al., "The Roles of Tyrosines 24,31, and 60 in the High Affinity Binding of Insulin-like Growth Factor-I to the Type 1 Insulin-like Growth Factor Receptor", The Journal of Biological Chemistry, vol. 265, No. 26, Issue of Sep. 15, pp. 15648-15652, 1990.

Bersell, et al., "Neuregulin1/ErbB4 signaling induces cardiomyocyte proliferation and repair of heart injury," Cell, 138:257-270, (Jul. 24, 2009).

Black, S., "In vivo models of myocardial ischemia and reperfusion injury: application to drug discovery and evaluation," J. Pharmacol. Toxicol. Methods 43(2):153-167, (Mar.-Apr. 2000).

Bock-Marquette, et al., "Thymosin B4 activates integrin-linked kinase and promotes cardiac cell migration, survival and cardiac repair," Nature, 432:466-472, (Nov. 25, 2004).

Buerke, et al., "Cardioprotective effect of insulin-like growth factor I in myocardial ischemia followed by reperfusion," Proc. Natl. Acad. Sci. USA, 92: 8031-8035, (Aug. 1995).

Bujak, 2007, Cardiovascular Research, vol. 74, Issue 2, pp. 184-195.

Burchfield, et al., "Interleukin-10 from transplanted bone marrow mononuclear cells contributes to cardiac protection after myocardial infarction," Circulation Research, 15 pages, (Mar. 23, 2011).

Burchfield, et al., "Role of paracrine factors in stem and progenitor cell mediated cardiac repair and tissue fibrosis," Fibrogenesis and Tissue Repair, 1(4):1-11, (2008).

Burchfield, et al., "The cytoprotective effects of tumor necrosis factor are conveyed through tumor necrosis factor receptor-associated factor 2 in the heart," Circulation Heart Failure, 16 pages, (Jan. 2010).

Burrill, Devin et al., "Targeted erythropoietin selectively stimulates red blood cell expansion in vivo", Proceedings of the National Academy of Sciences of the United States of America (PNAS), vol. 113, No. 19, pp. 5245-5250, May 10, 2016.

Chen, et al. "Effects of receptor binding on plasma half-life of bifunctional transferrin fusion proteins, "Molecular Pharmaceutics 8: 457-65 (2011).

Chen, et al., "Localization of monoclonal antibody TNT-1 in experimental kidney infarction of the mouse," FASEB J., 4(12):3033-3039, (Sep. 1, 1990).

Chimenti, et al., "Myocardial infarction: animal models," Methods. Mol. Med., 98:217-226, (2004).

Christman, et al., "Enhanced neovasculature formation in ischemic myocardium following delivery of pleiotrophin plasmid in a biopolymer,"Biomaterials, 26:1139-1144 (2005).

Cironi, Pablo et al., "Enhancement of Cell Type Specificity by Quantitative Modulation of Chimeric Ligand", The Journal of Biological Chemistry, vol. 283, No. 13, pp. 8460-8476, Mar. 28, 2008.

Davis, "Local myocardial insulin-like growth factor 1 (IGF-1) delivery with biotinylated peptide nanofibers improves cell therapy for myocardial infarction," Proc. Natl. Acad. Sci USA, 103(21):8155-8160, (May 23, 2006).

Davletov, A. & Sudhof, T., "A single C2 domain from synaptotagmin I is sufficient for high affinity Ca2+/phospholipid binding," J. Biol. Chem., 268(35):26386-2690, (Dec. 15, 1993).

Doldan-Martelli et al., "A Mathematical Model for the Rational Design of Chimeric Ligands in Selective Drug Therapies," CPT: Pharmacometrics & Systems Pharmacology (2013), 2, e26, Feb. 13, 2013.

Dorn II, M.D., "Periostin and myocardial repair, regeneration, and recovery," The New England Journal of Medicine, 357(15):1552-1554, (Oct. 11, 2007).

Dubaquie, Y. et al. "Total Alanine-Scanning Mutagenesis of Insulin-Like Growth Factor I (IGF-I) Identifies Differential Binding Epitopes for IGFBP-1 and IGFBP-3", Biochemistry, 1999, 38, 6386-6396.

Dumont, et al., "Cardiomyocyte Death Induced by Myocardial Ischemia and Reperfusion: Measurement With Recombinant Human Annexin-V in a Mouse Model ," Circulation 102(13):1564-1568, (Sep. 26, 2000).

Engel, et al., "FGF1/p38 MAP kinase inhibitor therapy induces cardiomyocyte mitosis, reduces scarring, and rescues function after myocardial infarction," PNAS, 103(42):15546-15551, (Oct. 17, 2006).

Epa, V.C. et al., "Model for the Complex between the insulin-like growth factor 1 and its receptors: towards designing antagonists for the IGF-1 receptor", Protein Engineering, Design & Selection, vol. 19, No. 8, pp. 377-384, 2006.

Francis, G.L., et al., "Novel recombinant fusion protein analogues of insulin-like growth factor (IGF)-I indicate the relative importance of IGF-binding protein and receptor binding for enhanced biological potency", Journal of Molecular Endocrinology (1992), 8, pp. 213-223.

GenBank: BAA78418.1, vascular endothelial growth factor isoform VEGF165 [*Homo sapiens*], NCBI Protein Database, GenBank: BAA78418.1 (Jun. 3, 1999), also available at http://www.ncbi.nlm.nih.gov/protein/BAA78418.1 (last visited Apr. 21, 2016).

(56) References Cited

OTHER PUBLICATIONS

George, et al., "Typhostin AG-556 reduces myocardial infarct size and improves cardiac performance in the rat," Experimental and Molecular Pathology, 74:314-318 (2003).
Gnecchi, et al., "Evidence supporting paracrine hypothesis for Akt-modified mesenchymal stem cell-mediated cardiac protection and functional improvement," The FASEB Journal, 20:661-669, (Apr. 2006).
Gnecchi, et al., "Paracrine mechanisms in adult stem cell signaling and therapy," Adult Stem Cells and Paracrine Effects, 1204-1219, (Nov. 2008).
Greenberg, et al., "Chapter 7. Mouse models of ischemic angiogenesis and ischemia-reperfusion injury," Methods Enzymol., 444:159-174, (2008).
Gripenberg, et al., "A Solid Phase Enzyme-linked Immunosorbent Assay (ELISA) for the Demonstration of Antibodies against Denatured, Single-stranded DNA in Patient Sera," Scand. J. Immunol., 7(2):151-157, (Feb. 1978).
Han, et al., "Refolding of a recombinant collagen-targeted TGF-B2 fusion protein expressed in *Escherichia coli*," Protein Expression and Purification, 11:169-178 (1997).
Hashino, K., et al., "A 31-kDa Recombinant Fibronectin Cell-Binding Domain Fragment: Its Binding to Receptor, Cell Adhesive Activity, and Fusion Proteins," J. Biochem., 119(4):604-609, (Apr. 4, 1996).
Hausenloy et al., "Cardioprotective growth factors," Cardiovascular Research, 83: 179-194, (2009).
Hefta, et al., "Measuring Affinity Using Biosensors", in "Antibody engineering: A Practical Approach", pp. 99-116, Oxford University Press, 1996, Edited by McCafferty et al., (Hames B.D.eds).
Henson, 2006, Cellular Signaling, vol. 18, pp. 2089-2097.
Hinkel et al., "Thymosin B4 is an essential paracrine factor of embryonic endothelial progenitor cell-mediated cardioprotection," Circulation, 2232-2240 (Apr. 29, 2008).
Hoberg, E., et al., "Monoclonal antibodies specific for human cardiac myosin: selection, characterization and experimental myocardial infarct imaging," Eur Heart J., 9(3):328-236, (Mar. 1988).
Hofstra, et al., "Visualisation of cell death in vivo in patients with acute myocardial infarction," The Lancet, 356(9225):209-212, (2000).
Hsieh et al., "Local controlled intramyocardial delivery of plateet-derived growth factor improves postinfarction ventricular function without pulmonary toxicity," Circulation, 637-644, (Aug. 15, 2006).
Hu et al., Stromal cell-derived factor-1a confers protection against myocardial ischemia/reperfusion injury, Molecular Cardiology, 654-663, (Aug. 7, 2007).
Ieda, et al., "Cardiac fibroblasts regulate myocardial proliferation through B1 integrin signaling," Developmental Cell, 16: 233-244 (Feb. 17, 2009).
Igarashi, K., et al., "Specific binding of a synthetic peptide derived from an antibody complementarity determining region to phosphatidylserine," J Biochem., 117(2):452-457, (Feb. 1995).
Ishikawa, et al., "Production of biologically active epidermal growth factor fusion protein with high collagen affinity," J. Biochem., 129(4): 627-633 (2001).
Jeon, et al., "Long-term and zero-order release of basic fibroblast growth factor from heparin-conjugated poly(L-lactide-co-glycolide) nanospheres and fibrin gel," Biomaterials, 27:1598-1607 (2006).
Kanashiro-Takeuchi, et al., "Cardioprotective effects of growth hormone-releasing hormone agonist after myocardial infarction," PNAS, 107(6):2604-2609, (Feb. 9, 2010).
Kardami, et al., "Fibroblast growth factor-2 and cardioprotection," Heart Fail Rev., 12:267-277 (2007).
Kawase Y. et al. "Construction and characterization of a fusion protein with epidermal growth factor and the cell-binding domain of fibronectin" FEBS letters, 298(2-3),: 126-128, 1992.
Kenis et al., "Annexin A5: shifting from a diagnostic towards a therapeutic realm", Cellular Molecular Life Sciences, vol. 64, pp. 2859-2862, ePub Sep. 17, 2007.
Kenis, H., et al., "Annexin A5 uptake in ischemic myocardium: demonstration of reversible phosphatidylserine externalization and feasibility of radionuclide imaging," J Nucl Med., 51(2):259-67, (Feb. 2010).
Kenis, H., et al., "Cell surface-expressed phosphatidylserine and annexin A5 open a novel portal of cell entry," J Biol Chem., 279(50):52623-52629, Epub Sep. 20, 2004, (Dec. 10, 2004).
Khaw, B., et al., "Monoclonal antibody to cardiac myosin: imaging of experimental myocardial infarction," Hybridoma, 3(1):11-23, (1984).
King et al., "Production and characterization of recombinant insulin-like growth factor-I (IGF-I) and potent analogues of IGF-I, with Gly or Arg substituted for Glu3, following their expression in *Escherichia colu* as fusion proteins", Journal of Molecular Endocrinology, (1992) 8, pp. 29-41.
Klopsch, et al., "Intracardiac injection of erythropoietin induces stem cell recruitment and improves cardiac functions in a rat myocardial infarction model," J. Cell. Mol. Med. 13(4): 664-679, (2009).
Ko, Y., et al., "Gene delivery into ischemic myocardium by double-targeted lipoplexes with anti-myosin antibody and TAT peptide," Gene Ther., 16(1):52-9. Epub Aug. 14, 2008, (Jan. 2009).
Kobayashi, et al., "Effect of atrial natriuretic peptide on ischemia-reperfusion injury in a porcine total hepatic vascular exclusion model," World J. Gastroenterol., 13(25):3487-3492, (Jul. 7, 2007).
Kuhn, et al., "Periostin induces proliferation of differentiated cardiomyocytes and promotes cardiac repair," Nature Medicine, 13(8):962-969, (Aug. 2007).
Kuramochi, "Cardiac Endothelial Cells Regulate Reactive Oxygen Species-induced Cardiomyocyte Apoptosis through Neuregulin-1_/erbB4 Signaling*," J. Biol. Chem., 279(49): 51141-51147, (2004).
Laajoki, L. et al. Solution Structure and Backbone Dynamics of Long-[ARG3] Insulin-like Growth Factor-I; Journal of Biological Chemistry, vol. 275, No. 14, pp. 10009-10015, Apr. 7, 2000.
Laroche-Traineau, J., et al., "A human monoclonal antibody obtained from EBV-transformed B cells with specificity for myosin," Br J Haematol., 91(4):951-962, (Dec. 1995).
Laroche-Traineau, J., et al., "Analysis of the V genes coding for a monospecific human antibody to myosin and functional expression of single chain Fv fragments," FEBS Lett., 460(1):86-92, (Oct. 22, 1999).
Laroche-Traineau, J., et al., "Three-step purification of bacterially expressed human single-chain Fv antibodies for clinical applications," J Chromatogr B Biomed Sci Appl., 737(1-2):107-117, (Jan. 14, 2000).
Liang, W., et al., "ATP-containing immunoliposomes specific for cardiac myosin," Curr Drug Deliv., 1(1):1-7, (Jan. 2004).
Liu, et al., "Neuregulin-1/erbB-activation improves cardiac function and survival in models of ischemic, dilated, and viral cardiomyopathy," Journal of the American College of Cardiology, 48(7):1438-1447, (Oct. 3, 2006).
Loddick, S. et al., "Displacement of insulin-like growth factors from their binding proteins as a potential treatment for stroke", PNAS, vol. 95, pp. 1894-1898, Feb. 1998.
Lorts, et al., "Genetic manipulation of periostin expression in the heart does not affect myocyte content, cell cycle activity, or cardiac repair," UltraRapid Communication, e1-e7, (Jan. 2, 2009).
Marshall, K.W. & Marks, J.D. "Engineering and characterization of a novel fusion protein incorporating B7.2 and an anti-ErbB-2 single-chain antibody fragment for the activation of Jurkat T cells," Journal of Immunotherapy. Hagerstown, Md. : 1997) 24: 27-36 (2001).
Mihardja, et al., "Targeted in vivo extracellular matrix formation promotes neovascularization in a rodent model of myocardial infarction," PLoS One, 5(4):e10384 (8 pages), (Apr. 2010).
Mira, et al., "Inhibition of cytosolic phospholipase A2 by annexin V in differentiated permeabilized HL-60 cells. Evidence of crucial importance of domain I type II Ca2+-binding site in the mechanism of inhibition," J. Biol Chem., 272(16):10474-10482, (Apr. 18, 1997).

(56) References Cited

OTHER PUBLICATIONS

Miranda, et al., "Endothelium-dependent and -independent hepatic artery vasodilatation is not impaired in a canine model of liver ischemia-reperfusion injury," Braz. J. Med. Biol. Res., 40(6):857-865, (Jun. 2007).
Murray and Brown, "Measurement of association constants in ELISA. Reactions between solid-phase antibody and fluid-phase biotinylated antigen," J. Immunol. Methods., 127(1):25-28 (Feb. 20, 1990).
Nedelman, M., et al., "Rapid infarct imaging with a technetium-99m-labeled antimyosin recombinant single-chain Fv: evaluation in a canine model of acute myocardial infarction," J Nucl Med., 34(2):234-241, (Feb. 1993).
Nelson, P., et al. "Characterization of anti-myosin monoclonal antibodies," Hybridoma (Larchmt), 24(6):314-318, (Dec. 2005).
Nimni, "Polypeptide growth factors: targeted delivery systems," Biomaterials, 18(18):1201-1225, (1997).
Nishi, et al., "Collagen-binding growth factors: Production and characterization of functional fusion proteins having a collagen-binding domain," Proc. Natl. Acad. Sci. USA, 95:7018-7023, (Jun. 1998).
Novo Nordisk Pharmatech A/S "How Insulin and IGF-1 Bind to the receptors" retrieved from http://novonordiskpharmatech.com/how-insulin0and-igf-1-bind-to-their-receptors/ ; retrieved Dec. 16, 2016.
O' Sullivan et al., "Potent Long-Term Cardioprotective Effects of Single Low-Dose Insulin-Like Growth Factor-1 Treatment Postmyocardial Infarction", American Heart Association—Circulation: Cardiovascular Interventions, 4:327-335, Jun. 28, 2011.
Pak, K., et al., "An instant kit method for labeling antimyosin Fab' with technetium-99m: evaluation in an experimental myocardial infarct model," J. Nucl Med., 33(1):144-149, (Jan. 1992).
Peter, K., et al., "Construction and functional evaluation of a single-chain antibody fusion protein with fibrin targeting and thrombin inhibition after activation by factor Xa," Circulation, 101(10):1158-1164, (Mar. 14, 2000).
Pietronave, et al., "Agonist monoclonal antibodies against HGF receptor protect cardiac muscle cells from apoptosis," Am J Physiol Heart circ Physiol, 298:H1155-H1165, (2010).
Prior, et al. "Cytotoxic Activity of a Recombinant Fusion Protein between Insulin-like Growth Factor I and Pseudomonas Exotoxin," Cancer, 174-180 (1991).
Rosenthal, et al., "Growth factor enhancement of cardiac regeneration," Cell Transplantation, 15(1):S41-S45, (2006).
Saxena, et al., "Stromal cell-derived factor-1a is cardioprotective after mocardial infarction," Molecular Cardiology, 2224-2231, (2008).
Schutters, K. & Reutelingsperger, C.P.M. "Phosphatidylserine targeting for diagnosis and treatment of human diseases," Apoptosis : An International Journal on Programmed Cell Death. 15:1072-82, (2010).
Scott, R.C. et al. "Targeted Delivery of Antibody Conjugated Liposomal Drug Carriers to Rat Myocardial Infarction," Biotechnology, 96:795-802, (2007).
Scott, et al. "Aiming for the heart: targeted delivery of drugs to diseased cardiac tissue," Expert Opinion on Drug Delivery, 5:459-70, (2008).
Scott, R.C. et al. "Targeting VEGF-encapsulated immunoliposomes to MI heart improves vascularity and cardiac function". The FASEB Journal : Official Publication of the Federation of American Societies for Experimental Biology, 23:3361-7, (2009).
Segers, et al., "Protein therapeutics for cardiac regeneration after myocradial infarction," J. of Cardiovasc. Trans. Res., 9 pages, (Jul. 7, 2010).
Shan, et al., "Overexpression of TRPC3 increases apoptosis but not necrosis in response to ischemia-reperfusion in adult mouse cardiomyocytes," Am. J. Physiol. Cell. Physiol., 294(3):833-841, (Mar. 2008).
Shin, S.U. & Morrison, S.L., "Expression and characterization of an antibody binding specificity joined to insulin-like growth factor 1: potential applications for cellular targeting," Proceedings of the National Academy of Sciences of the United States of America, 87:5322-6, (1990).
Shin, et al. "Functional properties of antibody insulin-like growth factor fusion proteins," The Journal of Biological Chemistry, 269: 4979-8,5 (1994).
Simeonova, P., et al., "Identification of human ventricular myosin heavy chain fragments with monoclonal antibody 2F4 in human sera after myocardial necrosis," Clin Chim Acta., 201(3):207-221, (Sep. 30, 1991).
Stamm et al., Human ortholog to mouse gene imap38 encoding an ER-localized G-protein belongs to the gene family clustered on chromosome 7q32-36, Gene vol. 282: 159-167, 2003.
Stokes, et al., "A simple, rapid ELISA method for the detection of DNA antibodies," J. Clin. Pathol., 35(5):566-573, (May 1982).
Stowe, et al., Engineering Growth Factors For Cardiomyocyte Survival and Regeneration Following Ischemic Injury. American Heart Association Basic Cardiovascular Science [online Jul. 15, 2014 [retrieved Dec. 5, 2016].
Suleiman, et al., "Apoptosis and the cardiac action of insulin-like growth factor I," Pharmacology and Therapeutics, 114:278-294, (2007).
Sutton, R., et al., "Structure of the first C2 domain of synaptotagmin I: a novel Ca2+/phospholipid-binding fold," Cell, 80(6):929-938, (Mar. 24, 1995).
Tomas, F.M. et al., "IGF-I variants which bind poorly to IGF-binding proteins show more potent and prolonged hypoglycemic action that native IGF-I in pigs and marmoset monkeys", Journal of Endocrinology (1997), 155, 377-386.
Tuan et al., "Engineering, expression and renaturation of targeted TGF-beta fusion proteins"; Connect Tissue Res. 1996; 34(1):1-9.
Ueda, et al., "A potential cardioprotective role of hepatocyte growth factor in myocardial infarction in rats," Cardiovascular Research, 51:41-50, (2001).
Umeda, M., et al., "Effective production of monoclonal antibodies against phosphatidylserine: stereo-specific recognition of phosphatidylserine by monoclonal antibody," J Immunol., 143(7):2273-2279, (Oct. 1, 1989).
Ungethum, et al., "Engineered annexin A5 variants have impaired cell entry for molecular imaging of apoptosis using pretargeting strategies," J Biol Chem., 286(3):1903-10. Epub Nov. 15, 2010, (Jan. 21, 2011).
Urbanek K et al., "Myocardial regeneration by activation of multipotent cardiac stem cells in ischemic heart failure," Proc. Natl. Acad. Sci. USA, 102(24):8692-8697, (Jun. 14, 2005).
Wang, et al., "Degradable PLGA scaffolds with basic fibroblast growth factor," Texas Heart Institute Journal, 89-97, (2009).
Wassaf, et al., "High-throughput affinity ranking of antibodies using surface plasmon resonance microarrays," Anal. Biochem., 351(2):241-253, (Apr. 15, 2006).
Winter, et al. "A new bioassay for the immunocytokine L19-IL2 for simultaneous analysis of both functional moieties," Journal of Pharmaceutical and Biomedical Analysis, 54:81-6 (2011).
Yang L. et al., "Human cardiovascular progenitor cells develop from a KDR+ embryonic-stem-cell-derived population", Nature. May 22, 2008, 453(7194):524-8. Epub Apr. 23, 2008.
Yeghiazarians, et al., "Injection of bone marrow cell extract into infarcted hearts results in functional improvement comparable to intact cell therapy," The American Society of Gene Therapy, 17(7):1250-1256, (Jul. 2009).
Zaruba, et al., "Synergy between CD26/DPP-IV inhibition and G-CSF improves cardiac function after acute myocardial infarction," Cell Stem Cell, 4:313-323, (Apr. 3, 2009).
Zbinden, et al., "Interanimal variability in preexisting collaterals is a major factor determining outcome in experimental angiogenesis trials," Am. J. Physiol. Heart Circ. Physiol., 292(4): H1891-H1897, (Apr. 2007).
Zentilin, et al., "Cardiomyocyte VEGFR-1 activation by VEGF-B induces compensatory hypertrophy and preserves cardiac function after myocardial infarction," The FASEB Journal, 24:1467-1478, (May 2010).

(56) References Cited

OTHER PUBLICATIONS

Zhang, J. et al. "Collagen-targeting vascular endothelial growth factor improves cardiac performance after myocardial infarction," Circulation, 119:1776-84, (2009).
Zhao, et al., "Neuregulins promote survival and growth of cardiac myocytes," The Journal of Biological Chemistry, 273(17):0261-10269, (Apr. 24, 1998).
Zhao, Ming, et al., 99m Tc-Labeled C2A Domain of Synaptotagmin I as a Target-Specific Molecular Probe for Noninvasive Imaging of Acute Myocardial Infarction, The Journal of Nuclear Medicine, vol. 47, No. 8, Aug. 2006, pp. 1367-1374.
Zhao, et al., "Recruitment of endogenous stem cells for tissue repair," Macromolecular Bioscience, 8:836-842, (2008).
Ziegler m. et al., "The bispecific SDF1-GPVI fusion protein preserves myocardial function after transient ischemia in mice" Circulation Feb. 7, 2012; 125(5): 685-96. Doi: 10.1161/Circulation.111.070508.Epub Jan. 5, 2012.
International Search Report based on PCT/2011/037459, mailed Aug. 30, 2011.
Bork, Peer, Powers and Pitfalls in Sequence Analysis: The 70% Hurdle, Genome Research, vol. 10, Issue 4, pp. 398-400 (2000).
Botusan et al., "Deficiency of liver-derived insulin-like growth factor-I (IGF-I) does not interfere with the skin wound healing rate", PLOS One, vol. 13, No. 3, e0193084, Mar. 13, 2018.
Bowie et al., "Deciphering the Message in Protein Sequences: Tolerance to Amino Acid Substitutions", Science, vol. 247, Issue 4948, pp. 1306-1310, Mar. 16, 1990.
Burgess et al., "Possible dissociation of the heparin-binding and mitogenic activities of heparin-binding (acidic fibroblast) growth factor-1 from its receptor-binding activities by site-directed mutagenesis of a single lysine residue", Journal of Cell Biology, vol. 111, Issue 5, pp. 2129-2138, Nov. 1, 1990.
Greenspan et al., "Defining epitopes: It's not as easy as it seems", Nature Biotechnology, vol. 17, pp. 936-937 (1999).
Kineman, R.D., et al., "40 Years of IGF1 Understanding the tissue-specific roles of IGF1/IGF1R in regulating metabolism using the Cre/IoxP system", Journal of Molecular Endocrinology, 61(1), pp. T187-T198, (2018).
Lazar et al., "Transforming Growth Factor a: Mutation of Aspartic Acid 47 and Leucine 48 Results in Different Biological Activities", Molecular and Cellular Biology, vol. 8, Issue 3, pp. 1247-1252, Mar. 1988.
Osborn et al., "Albutropin: a growth hormone-albumin fusion with improved pharmacokinetics and pharmacodynamics in rats and monkeys", European Journal of Pharmacology, vol. 456, Issue 1-3, pp. 149-158, Dec. 5, 2002.

* cited by examiner

SEQUENCE LISTING

```
Sequence total quantity: 49
SEQ ID NO: 1           moltype = AA  length = 249
FEATURE                Location/Qualifiers
```

```
REGION                1..249
                      note = Synthetic construct
source                1..249
                      mol_type = protein
                      organism = synthetic construct
SEQUENCE: 1
LESGGGLVQP GGSLRLSCAG SGFTFSSYAM SWVRQAPGKG LEWVSSISGS GGSTYYADSV  60
KGRFTISRDN SKKTLYLQMN SLRAEDTAVY YCARKRGRTT VSWGLVYFDY WGQGTVVTVS  120
SGGGGSGGGG SGGGGSGGGG SGGSELTQSP GTLSLSPGER ATLSCRASHS VSRAYLAWYQ  180
QKPGQAPRLL IYGTSSRATG IPDRFSGSGS GTDFTLTISR LEPEDFAVYY CQQYGGSPWF  240
GQGTKVELK                                                          249

SEQ ID NO: 2          moltype = AA  length = 251
FEATURE               Location/Qualifiers
REGION                1..251
                      note = Synthetic construct
source                1..251
                      mol_type = protein
                      organism = synthetic construct
SEQUENCE: 2
LEQSGGGVVQ PGGSLRLSCT ASGFTFSSYG MHWVRQAPGK GLEWVTFIRY DGSSKYSADS  60
VKGRFTISRD NSKNTLFLQM NSLRAEDTAV YYCARARWRD YYYYMDVWGK GTTVTVSSGG  120
GGSGGGGSGG GGSGGGGSGG SELTQEPSVS GAPGQRVTIS CTGSSSNIGA GYDVHWYQQL  180
PGTAPKLLIY GNSNRPSGVP DRFSGSKSGT SASLAITGLQ AEDEADYYCQ SYDSSLSGVV  240
FGGGTKLTVL G                                                       251

SEQ ID NO: 3          moltype = AA  length = 70
FEATURE               Location/Qualifiers
source                1..70
                      mol_type = protein
                      organism = Homo sapiens
SEQUENCE: 3
GPETLCGAEL VDALQFVCGD RGFYFNKPTG YGSSSRRAPQ TGIVDECCFR SCDLRRLEMY  60
CAPLKPAKSA                                                         70

SEQ ID NO: 4          moltype = AA  length = 70
FEATURE               Location/Qualifiers
REGION                1..70
                      note = Synthetic construct
source                1..70
                      mol_type = protein
                      organism = synthetic construct
SEQUENCE: 4
GPETLCGAEL VAALQFVCGD RGFYFNKPTG YGSSSRRAPQ TGIVDECCFR SCDLRRLEMY  60
CAPLKPAKSA                                                         70

SEQ ID NO: 5          moltype = AA  length = 70
FEATURE               Location/Qualifiers
REGION                1..70
                      note = Synthetic construct
source                1..70
                      mol_type = protein
                      organism = synthetic construct
SEQUENCE: 5
GPETLCGAAL VDALQFVCGD RGFYFNKPTG YGSSSRRAPQ TGIVDECCFR SCDLRRLEMY  60
CAPLKPAKSA                                                         70

SEQ ID NO: 6          moltype = AA  length = 179
FEATURE               Location/Qualifiers
REGION                1..179
                      note = Synthetic construct
source                1..179
                      mol_type = protein
                      organism = synthetic construct
SEQUENCE: 6
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNCIIG KGRSYKGTVS ITKSGIKCQP  120
WSSMIPHEHS FLPSSYRGKD LQENYCRNPR GEEGGPWCFT SNPEVRYEVC DIPQCSEVE   179

SEQ ID NO: 7          moltype = AA  length = 88
FEATURE               Location/Qualifiers
REGION                1..88
                      note = Synthetic construct
source                1..88
                      mol_type = protein
                      organism = synthetic construct
SEQUENCE: 7
DYIRNCIIGK GRSYKGTVSI TKSGIKCQPW SSMIPHEHSF LPSSYRGKDL QENYCRNPRG  60
EEGGPWCFTS NPEVRYEVCD IPQCSEVE                                     88
```

```
SEQ ID NO: 8            moltype = AA  length = 193
FEATURE                 Location/Qualifiers
REGION                  1..193
                        note = HGF alpha chain N-K2 fusion
source                  1..193
                        mol_type = protein
                        organism = synthetic construct
SEQUENCE: 8
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNSEVE CMTCNGESYR GLMDHTESGK  120
ICQRWDHQTP HRHKFLPERY PDKGFDDNYC RNPDGQPRPW CYTLDPHTRW EYCAIKTCAD  180
NTMDTDVPLE TTE                                                     193

SEQ ID NO: 9            moltype = AA  length = 97
FEATURE                 Location/Qualifiers
REGION                  1..97
                        note = Synthetic construct
source                  1..97
                        mol_type = protein
                        organism = synthetic construct
SEQUENCE: 9
SEVECMTCNG ESYRGLMDHT ESGKICQRWD HQTPHRHKFL PERYPDKGFD DNYCRNPDGQ  60
PRPWCYTLDP HTRWEYCAIK TCADNTMDTD VPLETTE                           97

SEQ ID NO: 10           moltype = AA  length = 585
FEATURE                 Location/Qualifiers
REGION                  1..585
                        note = Synthetic construct
source                  1..585
                        mol_type = protein
                        organism = synthetic construct
SEQUENCE: 10
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 11           moltype = DNA  length = 1755
FEATURE                 Location/Qualifiers
misc_feature            1..1755
                        note = Synthetic construct
source                  1..1755
                        mol_type = other DNA
                        organism = synthetic construct
SEQUENCE: 11
gacgctcaca agagcgaagt ggcacatagg ttcaaagatc tgggcgaaga gaactttaag  60
gccctcgtcc tgatcgcttt cgcacagtac ctccagcagt ctccctttga agatcacgtg  120
aaactggtca atgaggtgac cgaatttgcc aagacatgcg tggctgatga gagtgcagaa  180
aactgtgaca aatcactgca tactctcttt ggagataagc tgtgcaccgt cgccacactc  240
agagagactt atggggaaat ggctgactgt tgcgcaaaac aggagcctga acggaatgag  300
tgtttcctcc agcacaagga tgacaaccca aatctgcccc gcctcgtgcg acctgaggtc  360
gatgtgatgt gcaccgcctt tcatgacaac gaagagacat tcctgaagaa atacctgtat  420
gaaattgctc gtaggcaccc atacttttat gcccccgagc tcctgttctt tgcaaagaga  480
tacaaagctg ccttcactga atgttgccag gcagctgata aggccgcatg tctcctgcct  540
aaactggacg agctccggga tgaaggtaag gcttccagcg ccaaacagcg cctgaagtgc  600
gcttctctcc agaagtttgg cgagcgagca ttcaaagcct gggctgtggc ccgtctcagt  660
cagaggtttc caaaggcaga atttgctgag gtctcaaaac tggtgaccga cctcacaaag  720
gtccatactg agtgttgcca cggagatctg ctggaatgtg ccgacgatag agcagacctc  780
gctaaatata tctgcgagaa tcaggattcc attagctcta agctgaaaga atgttgcgag  840
aagcccctcc tggaaaagag tcattgtatc gccgaggtgg aaaacgacga gatgccagca  900
gatctgccat cactcgctgc cgactttgtg gaatccaaag atgtctgcaa gaattacgca  960
gaggctaaag acgtgttcct ggggatgttt ctgtatgagt acgcccggcg tcaccccgat  1020
tatagcgtcg tgctcctgct ccgactggca aagacctacg aaacaactct ggagaaatgt  1080
tgcgctgccg cagaccctca tgaatgttat gctaaggtgt tcgatgagtt taagccactc  1140
gtcgaagagc cccagaacct gattaaacag aattgcgaac tgttcgagca gctcggtgaa  1200
tacaagtttc agaacgccct gctcgtgcgt tataccaaaa aggtccctca ggtgtctaca  1260
ccaactctgg tggaggtcag taggaatctg ggcaaagtgg gatcaaagtg ttgcaaacac  1320
cccgaggcaa agagaatgcc ttgtgctgaa gattacctct ccgtcgtgct gaaccagctc  1380
tgcgtgctgc atgaaaagac cccagtcagc gatcgggtga caaaatgttg caccgaatct  1440
ctggtcaatc gccgaccctg tttcagtgcc ctcgaagtgg acgaaactta tgtgcctaag  1500
gagtttcagg ctgaaacatt cacctttcac gccgatatct gcactctgtc cgagaaagaa  1560
aggcagatta agaaacagac agcactggtc gagctcgtga agcataaacc aaaggctacc  1620
```

```
aaggagcagc tgaaagccgt catggacgat ttcgcagctt ttgtggaaaa gtgttgcaaa  1680
gccgacgata aggagacttg tttcgcagaa gaggggaaaa agctcgtggc tgccagccag  1740
gcagctctgg gtctg                                                   1755

SEQ ID NO: 12          moltype = AA  length = 585
FEATURE                Location/Qualifiers
source                 1..585
                       mol_type = protein
                       organism = Homo sapiens
SEQUENCE: 12
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 13          moltype = DNA  length = 1755
FEATURE                Location/Qualifiers
source                 1..1755
                       mol_type = other DNA
                       organism = Homo sapiens
SEQUENCE: 13
gatgcacaca agagtgaggt tgctcatcgg tttaaagatt tgggagaaga aaatttcaaa  60
gccttggtgt tgattgcctt tgctcagtat cttcagcagt gtccatttga agatcatgta  120
aaattagtga atgaagtaac tgaatttgca aaaacatgtg tagctgatga gtcagctgaa  180
aattgtgaca aatcacttca tacccttttt ggagacaaat tatgcacagt tgcaactctt  240
cgtgaaacct atggtgaaat ggctgactgc tgtgcaaaac aagaacctga gagaaatgaa  300
tgcttcttgc aacacaaaga tgacaaccca aacctccccc gattggtgag accagaggtt  360
gatgtgatgt gcactgcttt tcatgacaat gaagagacat tttgaaaaa atacttatat  420
gaaattgcca gaagacatcc ttacttttat gccccggaac tccttttctt tgctaaaagg  480
tataaagctg cttttacaga atgttgccaa gctgctgata aagctgcctg cctgttgcca  540
aagctcgatg aacttcggga tgaagggaag gcttcgtctg ccaaacagag actcaaatgt  600
gccagtctcc aaaaatttgg agaaagagct ttcaaagcat gggcagtggc tcgcctgagc  660
cagagatttc ccaaagctga gtttgcagaa gtttccaagt tagtgacaga tcttaccaaa  720
gtccacacgg aatgctgcca tggagatctg cttgaatgtg ctgatgacag ggcggacctt  780
gccaagtata tctgtgaaaa tcaggattcg atctccagta aactgaagga atgctgtgaa  840
aaacctctgt tggaaaaatc ccactgcatt gccgaagtgg aaaatgatga gatgcctgct  900
gacttgcctt cattagctgc tgattttgtt gaaagtaagg atgtttgcaa aaactatgct  960
gaggcaaagg atgtcttcct gggcatgttt ttgtatgaat atgcaagaag gcatcctgat  1020
tactctgtcg tgctgctgct gagacttgcc aagacatatg aaaccactct agagaagtgc  1080
tgtgccgctg cagatcctca tgaatgctat gccaaagtgt tcgatgaatt taaacctctt  1140
gtggaagagc ctcagaattt aatcaaacaa aactgtgagc tttttaagca gcttggagag  1200
tacaaattcc agaatgcgct attagttcgt tacaccaaga aagtacccca agtgtcaact  1260
ccaactcttg tagaggtctc aagaaaccta ggaaaagtgg gcagcaaatg ttgtaaacat  1320
cctgaagcaa aaagaatgcc ctgtgcagaa gactatctat ccgtggtcct gaaccagtta  1380
tgtgtgttgc atgagaaaac gccagtaagt gacagagtca caaaatgctg cacagagtcc  1440
ttggtgaaca ggcgaccatg cttttcagct ctggaagtcg atgaaacata cgttcccaaa  1500
gagtttaatg ctgaaacatt caccttccat gcagatatat gcacactttc tgagaaggag  1560
agacaaatca agaaacaaac tgcacttgtt gagcttgtga aacacaagcc caaggcaaca  1620
aaagagcaac tgaaagctgt tatggatgat ttcgcagctt ttgtagagaa gtgctgcaag  1680
gctgacgata aggagacctg ctttgccgag gagggtaaaa aacttgttgc tgcaagtcaa  1740
gctgccttag gctta                                                   1755

SEQ ID NO: 14          moltype = AA  length = 588
FEATURE                Location/Qualifiers
REGION                 1..588
                       note = Synthetic construct
source                 1..588
                       mol_type = protein
                       organism = synthetic construct
SEQUENCE: 14
AASDAHKSEV AHRFKDLGEE NFKALVLIAF AQYLQQSPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFQAETF TFHADICTLS EKERQIKKQT ALVELVKHKP  540
KATKEQLKAV MDDFAAFVEK CCKADDKETC FAEEGKKLVA ASQAALGL                588

SEQ ID NO: 15          moltype = AA  length = 588
FEATURE                Location/Qualifiers
```

```
REGION                 1..588
                       note = Synthesized
source                 1..588
                       mol_type = protein
                       organism = synthetic construct
SEQUENCE: 15
AAQDAHKSEV AHRFKDLGEE NFKALVLIAF AQYLQQSPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFQAETF TFHADICTLS EKERQIKKQT ALVELVKHKP  540
KATKEQLKAV MDDFAAFVEK CCKADDKETC FAEEGKKLVA ASQAALGL              588

SEQ ID NO: 16          moltype = AA  length = 589
FEATURE                Location/Qualifiers
REGION                 1..589
                       note = Synthetic construct
source                 1..589
                       mol_type = protein
                       organism = synthetic construct
SEQUENCE: 16
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGLAAAL              589

SEQ ID NO: 17          moltype = AA  length = 592
FEATURE                Location/Qualifiers
REGION                 1..592
                       note = Synthetic construct
source                 1..592
                       mol_type = protein
                       organism = synthetic construct
SEQUENCE: 17
AASDAHKSEV AHRFKDLGEE NFKALVLIAF AQYLQQSPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFQAETF TFHADICTLS EKERQIKKQT ALVELVKHKP  540
KATKEQLKAV MDDFAAFVEK CCKADDKETC FAEEGKKLVA ASQAALGLAA AL           592

SEQ ID NO: 18          moltype = AA  length = 592
FEATURE                Location/Qualifiers
REGION                 1..592
                       note = Synthetic construct
source                 1..592
                       mol_type = protein
                       organism = synthetic construct
SEQUENCE: 18
AAQDAHKSEV AHRFKDLGEE NFKALVLIAF AQYLQQSPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFQAETF TFHADICTLS EKERQIKKQT ALVELVKHKP  540
KATKEQLKAV MDDFAAFVEK CCKADDKETC FAEEGKKLVA ASQAALGLAA AL           592

SEQ ID NO: 19          moltype = AA  length = 588
FEATURE                Location/Qualifiers
REGION                 1..588
                       note = Synthetic construct
source                 1..588
```

```
                         mol_type = protein
                         organism = synthetic construct
SEQUENCE: 19
AASDAHKSEV AHRFKDLGEE NFKALVLIAF AQYLQQCPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGL               588

SEQ ID NO: 20            moltype = AA  length = 588
FEATURE                  Location/Qualifiers
REGION                   1..588
                         note = Synthesized
source                   1..588
                         mol_type = protein
                         organism = synthetic construct
SEQUENCE: 20
AAQDAHKSEV AHRFKDLGEE NFKALVLIAF AQYLQQCPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGL               588

SEQ ID NO: 21            moltype = AA  length = 589
FEATURE                  Location/Qualifiers
REGION                   1..589
                         note = Synthetic construct
source                   1..589
                         mol_type = protein
                         organism = synthetic construct
SEQUENCE: 21
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLAAAL              589

SEQ ID NO: 22            moltype = AA  length = 592
FEATURE                  Location/Qualifiers
REGION                   1..592
                         note = Synthetic construct
source                   1..592
                         mol_type = protein
                         organism = synthetic construct
SEQUENCE: 22
AASDAHKSEV AHRFKDLGEE NFKALVLIAF AQYLQQCPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGLAA AL           592

SEQ ID NO: 23            moltype = AA  length = 592
FEATURE                  Location/Qualifiers
REGION                   1..592
                         note = Synthetic construct
source                   1..592
                         mol_type = protein
                         organism = synthetic construct
SEQUENCE: 23
```

-continued

```
AAQDAHKSEV AHRFKDLGEE NFKALVLIAF AQYLQQCPFE DHVKLVNEVT EFAKTCVADE  60
SAENCDKSLH TLFGDKLCTV ATLRETYGEM ADCCAKQEPE RNECFLQHKD DNPNLPRLVR  120
PEVDVMCTAF HDNEETFLKK YLYEIARRHP YFYAPELLFF AKRYKAAFTE CCQAADKAAC  180
LLPKLDELRD EGKASSAKQR LKCASLQKFG ERAFKAWAVA RLSQRFPKAE FAEVSKLVTD  240
LTKVHTECCH GDLLECADDR ADLAKYICEN QDSISSKLKE CCEKPLLEKS HCIAEVENDE  300
MPADLPSLAA DFVESKDVCK NYAEAKDVFL GMFLYEYARR HPDYSVVLLL RLAKTYETTL  360
EKCCAAADPH ECYAKVFDEF KPLVEEPQNL IKQNCELFEQ LGEYKFQNAL LVRYTKKVPQ  420
VSTPTLVEVS RNLGKVGSKC CKHPEAKRMP CAEDYLSVVL NQLCVLHEKT PVSDRVTKCC  480
TESLVNRRPC FSALEVDETY VPKEFNAETF TFHADICTLS EKERQIKKQT ALVELVKHKP  540
KATKEQLKAV MDDFAAFVEK CCKADDKETC FAEEGKKLVA ASQAALGLAA AL        592

SEQ ID NO: 24          moltype = AA  length = 197
FEATURE                Location/Qualifiers
REGION                 1..197
                       note = Synthetic construct
source                 1..197
                       mol_type = protein
                       organism = synthetic construct
SEQUENCE: 24
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQR                                                197

SEQ ID NO: 25          moltype = AA  length = 197
FEATURE                Location/Qualifiers
REGION                 1..197
                       note = Synthetic construct
source                 1..197
                       mol_type = protein
                       organism = synthetic construct
SEQUENCE: 25
GKASSAKQRL KCASLQKFGE RAFKAWAVAR LSQRFPKAEF AEVSKLVTDL TKVHTECCHG  60
DLLECADDRA DLAKYICENQ DSISSKLKEC CEKPLLEKSH CIAEVENDEM PADLPSLAAD  120
FVESKDVCKN YAEAKDVFLG MFLYEYARRH PDYSVVLLLR LAKTYETTLE KCCAAADPHE  180
CYAKVFDEFK PLVEEPQ                                                197

SEQ ID NO: 26          moltype = AA  length = 205
FEATURE                Location/Qualifiers
REGION                 1..205
                       note = Synthetic construct
source                 1..205
                       mol_type = protein
                       organism = synthetic construct
SEQUENCE: 26
VEEPQNLIKQ NCELFEQLGE YKFQNALLVR YTKKVPQVST PTLVEVSRNL GKVGSKCCKH  60
PEAKRMPCAE DYLSVVLNQL CVLHEKTPVS DRVTKCCTES LVNRRPCFSA LEVDETYVPK  120
EFQAETFTFH ADICTLSEKE RQIKKQTALV ELVKHKPKAT KEQLKAVMDD FAAFVEKCCK  180
ADDKETCFAE EGKKLVAASQ AALGL                                       205

SEQ ID NO: 27          moltype = AA  length = 197
FEATURE                Location/Qualifiers
REGION                 1..197
                       note = Synthetic construct
source                 1..197
                       mol_type = protein
                       organism = synthetic construct
SEQUENCE: 27
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQR                                                197

SEQ ID NO: 28          moltype = AA  length = 205
FEATURE                Location/Qualifiers
REGION                 1..205
                       note = Synthetic construct
source                 1..205
                       mol_type = protein
                       organism = synthetic construct
SEQUENCE: 28
VEEPQNLIKQ NCELFEQLGE YKFQNALLVR YTKKVPQVST PTLVEVSRNL GKVGSKCCKH  60
PEAKRMPCAE DYLSVVLNQL CVLHEKTPVS DRVTKCCTES LVNRRPCFSA LEVDETYVPK  120
EFNAETFTFH ADICTLSEKE RQIKKQTALV ELVKHKPKAT KEQLKAVMDD FAAFVEKCCK  180
ADDKETCFAE EGKKLVAASQ AALGL                                       205

SEQ ID NO: 29          moltype = AA  length = 609
FEATURE                Location/Qualifiers
source                 1..609
```

```
                        mol_type = protein
                        organism = Homo sapiens
SEQUENCE: 29
MKWVESIFLI FLLNFTESRT LHRNEYGIAS ILDSYQCTAE ISLADLATIF FAQFVQEATY  60
KEVSKMVKDA LTAIEKPTGD EQSSGCLENQ LPAFLEELCH EKEILEKYGH SDCCSQSEEG  120
RHNCFLAHKK PTPASIPLFQ VPEPVTSCEA YEEDRETFMN KFIYEIARRH PFLYAPTILL  180
WAARYDKIIP SCCKAENAVE CFQTKAATVT KELRESSLLN QHACAVMKNF GTRTFQAITV  240
TKLSQKFTKV NFTEIQKLVL DVAHVHEHCC RGDVLDCLQD GEKIMSYICS QQDTLSNKIT  300
ECCKLTTLER GQCIIHAEND EKPEGLSPNL NRFLGDRDFN QFSSGEKNIF LASFVHEYSR  360
RHPQLAVSVI LRVAKGYQEL LEKCFQTENP LECQDKGEEE LQKYIQESQA LAKRSCGLFQ  420
KLGEYYLQNA FLVAYTKKAP QLTSSELMAI TRKMAATAAT CCQLSEDKLL ACGEGAADII  480
IGHLCIRHEM TPVNPGVGQC CTSSYANRRP CFSSLVVDET YVPPAFSDDK FIFHKDLCQA  540
QGVALQTMKQ EFLINLVKQK PQITEEQLEA VIADFSGLLE KCCQGQEQEV CFAEEGQKLI  600
SKTRAALGV                                                          609

SEQ ID NO: 30           moltype = AA  length = 245
FEATURE                 Location/Qualifiers
REGION                  1..245
                        note = Synthetic construct
source                  1..245
                        mol_type = protein
                        organism = synthetic construct
SEQUENCE: 30
EVQLQQSGPE LVKPGASMKI SCKASGYSFT GYTMKWVKQS HGKNLEWIGL INPYNGGTSY  60
NQKFKGKATL TVDKSSSTAY MELLSLTSDD SAVYYCAREG DYDGAMDYWG QGTSVTVSGG  120
GGSGGGGSGG GGSGGGGSGG SDIQMTQSPS SLSASLGGKV TITCKSSQDI NKYIAWYQHK  180
PGKGPGLLIH YTSTLQPGIP SRFSGSGSGR DYSFSISNLD PENIAAYYCL QYDNLYTFGG  240
GTRLE                                                              245

SEQ ID NO: 31           moltype = AA  length = 319
FEATURE                 Location/Qualifiers
source                  1..319
                        mol_type = protein
                        organism = Homo sapiens
SEQUENCE: 31
AQVLRGTVTD FPGFDERADA ETLRKAMKGL GTDEESILTL LTSRSNAQRQ EISAAFKTLF  60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDAGIDEAQ VEQDAQALFQ  180
AGELKWGTDE EKFITIFGTR SVSHLRKVFD KYMTISGFQI EETIDRETSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGEDD                                               319

SEQ ID NO: 32           moltype = AA  length = 175
FEATURE                 Location/Qualifiers
REGION                  1..175
                        note = Synthetic construct
source                  1..175
                        mol_type = protein
                        organism = synthetic construct
SEQUENCE: 32
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNCIIG KGRSYKGTVS ITKSGIKCQP  120
WSSMIPHEHS FLPSSYRGKD LQENYCRNPR GEEGGPWCFT SNPEVRYEVC DIPQC       175

SEQ ID NO: 33           moltype = AA  length = 88
FEATURE                 Location/Qualifiers
REGION                  1..88
                        note = Synthetic construct
source                  1..88
                        mol_type = protein
                        organism = synthetic construct
SEQUENCE: 33
DYIRNCIIGK GRSYKGTVSI TKSGIKCQPW SSMIPHEHSF LPSSYRGKDL QENYCRNPRG  60
EEGGPWCFTS NPEVRYEVCD IPQCSEVE                                     88

SEQ ID NO: 34           moltype = AA  length = 193
FEATURE                 Location/Qualifiers
REGION                  1..193
                        note = Synthetic construct
source                  1..193
                        mol_type = protein
                        organism = synthetic construct
SEQUENCE: 34
QRKRRNTIHE FKKSAKTTLI KIDPALKIKT KKVNTADQCA NRCTRNKGLP FTCKAFVFDK  60
ARKQCLWFPF NSMSSGVKKE FGHEFDLYEN KDYIRNSEVE CMTCNGESYR GLMDHTESGK  120
ICQRWDHQTP HRHKFLPERY PDKGFDDNYC RNPDGQPRPW CYTLDPHTRW EYCAIKTCAD  180
NTMDTDVPLE TTE                                                     193

SEQ ID NO: 35           moltype = AA  length = 97
```

```
FEATURE                 Location/Qualifiers
REGION                  1..97
                        note = Synthetic construct
source                  1..97
                        mol_type = protein
                        organism = synthetic construct
SEQUENCE: 35
SEVECMTCNG ESYRGLMDHT ESGKICQRWD HQTPHRHKFL PERYPDKGFD DNYCRNPDGQ  60
PRPWCYTLDP HTRWEYCAIK TCADNTMDTD VPLETTE                           97

SEQ ID NO: 36           moltype = AA  length = 206
FEATURE                 Location/Qualifiers
REGION                  1..206
                        note = Synthetic construct
source                  1..206
                        mol_type = protein
                        organism = synthetic construct
SEQUENCE: 36
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQEKKSVRG  120
KGKGQKRKRK KSRYKSWSVY VGARCCLMPW SLPGPHPCGP CSERRKHLFV QDPQTCKCSC  180
KNTDSRCKAR QLELNERTCR CDKPRR                                       206

SEQ ID NO: 37           moltype = AA  length = 430
FEATURE                 Location/Qualifiers
REGION                  1..430
                        note = Synthetic construct
source                  1..430
                        mol_type = protein
                        organism = synthetic construct
SEQUENCE: 37
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQEKKSVRG  120
KGKGQKRKRK KSRYKSWSVY VGARCCLMPW SLPGPHPCGP CSERRKHLFV QDPQTCKCSC  180
KNTDSRCKAR QLELNERTCR CDKPRRASTG GGGSGGGGSG GGGSAPMAEG GGQNHHEVVK  240
FMDVYQRSYC HPIETLVDIF QEYPDEIEYI FKPSCVPLMR CGGCCNDEGL ECVPTEESNI  300
TMQIMRIKPH QGQHIGEMSF LQHNKCECRP KKDRARQEKK SVRGKGKGQK RKRKKSRYKS  360
WSVYVGARCC LMPWSLPGPH PCGPCSERRK HLFVQDPQTC KCSCKNTDSR CKARQLELNE  420
RTCRCDKPRR                                                         430

SEQ ID NO: 38           moltype = AA  length = 146
FEATURE                 Location/Qualifiers
REGION                  1..146
                        note = Synthetic construct
source                  1..146
                        mol_type = protein
                        organism = synthetic construct
SEQUENCE: 38
PALPEDGGSG AFPPGHFKDP KRLYCKNGGF FLRIHPDGRV DGVREKSDPH IKLQLQAEER  60
GVVSIKGVCA NRYLAMKEDG RLLASKCVTD ECFFFERLES NNYNTYRSRK YTSWYVALKR  120
TGQYKLGSKT GPGQKAILFL PMSAKS                                       146

SEQ ID NO: 39           moltype = AA  length = 65
FEATURE                 Location/Qualifiers
REGION                  1..65
                        note = Synthetic construct
source                  1..65
                        mol_type = protein
                        organism = synthetic construct
SEQUENCE: 39
SHLVKCAEKE KTFCVNGGEC FMVKDLSNPS RYLCKCQPGF TGARCTENVP MKVQNQEKAE  60
ELYQK                                                              65

SEQ ID NO: 40           moltype = AA  length = 222
FEATURE                 Location/Qualifiers
source                  1..222
                        mol_type = protein
                        organism = Homo sapiens
SEQUENCE: 40
SGKKPESAAG SQSPALPPRL KEMKSQESAA GSKLVLRCET SSEYSSLRFK WFKNGNELNR  60
KNKPQNIKIQ KKPGKSELRI NKASLADSGE YMCKVISKLG NDSASANITI VESNEIITGM  120
PASTEGAYVS SESPIRISVS TEGANTSSST STSTTGTSHL VKCAEKEKTF CVNGGECFMV  180
KDLSNPSRYL CKCQPGFTGA RCTENVPMKV QNQEKAEELY QK                     222

SEQ ID NO: 41           moltype = AA  length = 19
FEATURE                 Location/Qualifiers
REGION                  1..19
                        note = Synthetic construct
source                  1..19
```

```
                         mol_type = protein
                         organism = synthetic construct
SEQUENCE: 41
MGWSLILLFL VAVATRVLS                                                19

SEQ ID NO: 42            moltype = AA  length = 21
FEATURE                  Location/Qualifiers
REGION                   1..21
                         note = Synthetic construct
source                   1..21
                         mol_type = protein
                         organism = synthetic construct
SEQUENCE: 42
MAWRLWWLLL LLLLLWPMVW A                                             21

SEQ ID NO: 43            moltype = AA  length = 9
FEATURE                  Location/Qualifiers
REGION                   1..9
                         note = Synthetic construct
source                   1..9
                         mol_type = protein
                         organism = synthetic construct
SEQUENCE: 43
GGSHHHHHH                                                           9

SEQ ID NO: 44            moltype = AA  length = 11
FEATURE                  Location/Qualifiers
REGION                   1..11
                         note = Synthetic construct
source                   1..11
                         mol_type = protein
                         organism = synthetic construct
SEQUENCE: 44
GGSGGHHHHH H                                                        11

SEQ ID NO: 45            moltype = AA  length = 588
FEATURE                  Location/Qualifiers
REGION                   1..588
                         note = Synthetic construct
source                   1..588
                         mol_type = protein
                         organism = synthetic construct
SEQUENCE: 45
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFQAETFTFH ADICTLSEKE RQIKKQTALV ELVKHKPKAT  540
KEQLKAVMDD FAAFVEKCCK ADDKETCFAE EGKKLVAASQ AALGLAAA                588

SEQ ID NO: 46            moltype = AA  length = 592
FEATURE                  Location/Qualifiers
REGION                   1..592
                         note = Synthetic construct
source                   1..592
                         mol_type = protein
                         organism = synthetic construct
SEQUENCE: 46
GADAHKSEVA HRFKDLGEEN FKALVLIAFA QYLQQSPFED HVKLVNEVTE FAKTCVADES  60
AENCDKSLHT LFGDKLCTVA TLRETYGEMA DCCAKQEPER NECFLQHKDD NPNLPRLVRP  120
EVDVMCTAFH DNEETFLKKY LYEIARRHPY FYAPELLFFA KRYKAAFTEC CQAADKAACL  180
LPKLDELRDE GKASSAKQRL KCASLQKFGE RAFKAWAVAR LSQRFPKAEF AEVSKLVTDL  240
TKVHTECCHG DLLECADDRA DLAKYICENQ DSISSKLKEC CEKPLLEKSH CIAEVENDEM  300
PADLPSLAAD FVESKDVCKN YAEAKDVFLG MFLYEYARRH PDYSVVLLLR LAKTYETTLE  360
KCCAAADPHE CYAKVFDEFK PLVEEPQNLI KQNCELFEQL GEYKFQNALL VRYTKKVPQV  420
STPTLVEVSR NLGKVGSKCC KHPEAKRMPC AEDYLSVVLN QLCVLHEKTP VSDRVTKCCT  480
ESLVNRRPCF SALEVDETYV PKEFQAETFT FHADICTLSE KERQIKKQTA LVELVKHKPK  540
ATKEQLKAVM DDFAAFVEKC CKADDKETCF AEEGKKLVAA SQAALGLAAA LQ           592

SEQ ID NO: 47            moltype = AA  length = 592
FEATURE                  Location/Qualifiers
REGION                   1..592
                         note = Synthetid construct
source                   1..592
                         mol_type = protein
```

```
                          organism = synthetic construct
SEQUENCE: 47
GADAHKSEVA HRFKDLGEEN FKALVLIAFA QYLQQSPFED HVKLVNEVTE FAKTCVADES  60
AENCDKSLHT LFGDKLCTVA TLRETYGEMA DCCAKQEPER NECFLQHKDD NPNLPRLVRP  120
EVDVMCTAFH DNEETFLKKY LYEIARRHPY FYAPELLFFA KRYKAAFTEC CQAADKAACL  180
LPKLDELRDE GKASSAKQRL KCASLQKFGE RAFKAWAVAR LSQRFPKAEF AEVSKLVTDL  240
TKVHTECCHG DLLECADDRA DLAKYICENQ DSISSKLKEC CEKPLLEKSH CIAEVENDEM  300
PADLPSLAAD FVESKDVCKN YAEAKDVFLG MFLYEYARRH PDYSVVLLLR LAKTYETTLE  360
KCCAAADPHE CYAKVFDEFK PLVEEPQNLI KQNCELFEQL GEYKFQNALL VRYTKKVPQV  420
STPTLVEVSR NLGKVGSKCC KHPEAKRMPC AEDYLSVVLN QLCVLHEKTP VSDRVTKCCT  480
ESLVNRRPCF SALEVDETYV PKEFQAETFT FHADICTLSE KERQIKKQTA LVELVKHKPK  540
ATKEQLKAVM DDFAAFVEKC CKADDKETCF AEEGKKLVAA SQAALGLAAA TG          592

SEQ ID NO: 48             moltype = AA  length = 592
FEATURE                   Location/Qualifiers
REGION                    1..592
                          note = Synthetic construct
source                    1..592
                          mol_type = protein
                          organism = synthetic construct
SEQUENCE: 48
ASDAHKSEVA HRFKDLGEEN FKALVLIAFA QYLQQSPFED HVKLVNEVTE FAKTCVADES  60
AENCDKSLHT LFGDKLCTVA TLRETYGEMA DCCAKQEPER NECFLQHKDD NPNLPRLVRP  120
EVDVMCTAFH DNEETFLKKY LYEIARRHPY FYAPELLFFA KRYKAAFTEC CQAADKAACL  180
LPKLDELRDE GKASSAKQRL KCASLQKFGE RAFKAWAVAR LSQRFPKAEF AEVSKLVTDL  240
TKVHTECCHG DLLECADDRA DLAKYICENQ DSISSKLKEC CEKPLLEKSH CIAEVENDEM  300
PADLPSLAAD FVESKDVCKN YAEAKDVFLG MFLYEYARRH PDYSVVLLLR LAKTYETTLE  360
KCCAAADPHE CYAKVFDEFK PLVEEPQNLI KQNCELFEQL GEYKFQNALL VRYTKKVPQV  420
STPTLVEVSR NLGKVGSKCC KHPEAKRMPC AEDYLSVVLN QLCVLHEKTP VSDRVTKCCT  480
ESLVNRRPCF SALEVDETYV PKEFQAETFT FHADICTLSE KERQIKKQTA LVELVKHKPK  540
ATKEQLKAVM DDFAAFVEKC CKADDKETCF AEEGKKLVAA SQAALGLAAA LQ          592

SEQ ID NO: 49             moltype = AA  length = 592
FEATURE                   Location/Qualifiers
REGION                    1..592
                          note = Synthetic construct
source                    1..592
                          mol_type = protein
                          organism = synthetic construct
SEQUENCE: 49
ASDAHKSEVA HRFKDLGEEN FKALVLIAFA QYLQQSPFED HVKLVNEVTE FAKTCVADES  60
AENCDKSLHT LFGDKLCTVA TLRETYGEMA DCCAKQEPER NECFLQHKDD NPNLPRLVRP  120
EVDVMCTAFH DNEETFLKKY LYEIARRHPY FYAPELLFFA KRYKAAFTEC CQAADKAACL  180
LPKLDELRDE GKASSAKQRL KCASLQKFGE RAFKAWAVAR LSQRFPKAEF AEVSKLVTDL  240
TKVHTECCHG DLLECADDRA DLAKYICENQ DSISSKLKEC CEKPLLEKSH CIAEVENDEM  300
PADLPSLAAD FVESKDVCKN YAEAKDVFLG MFLYEYARRH PDYSVVLLLR LAKTYETTLE  360
KCCAAADPHE CYAKVFDEFK PLVEEPQNLI KQNCELFEQL GEYKFQNALL VRYTKKVPQV  420
STPTLVEVSR NLGKVGSKCC KHPEAKRMPC AEDYLSVVLN QLCVLHEKTP VSDRVTKCCT  480
ESLVNRRPCF SALEVDETYV PKEFQAETFT FHADICTLSE KERQIKKQTA LVELVKHKPK  540
ATKEQLKAVM DDFAAFVEKC CKADDKETCF AEEGKKLVAA SQAALGLAAA TG          592
```

BI-SPECIFIC FUSION PROTEINS

RELATED APPLICATIONS

This application is a continuation of U.S. application Ser. No. 17/078,978, filed Oct. 23, 2020, which is a divisional of U.S. application Ser. No. 15/957,252, filed Apr. 19, 2018, now U.S. Pat. No. 10,858,450, which is a divisional of U.S. application Ser. No. 14/187,728, filed Feb. 24, 2014, now U.S. Pat. No. 9,982,060, which is a divisional application of U.S. application Ser. No. 13/112,907, filed May 20, 2011, now U.S. Pat. No. 8,691,771, which claims the benefit of and priority to U.S. Provisional Application Ser. No. 61/347,040, filed May 21, 2010, the entire content of each of which is herein incorporated by reference in their entirety.

REFERENCE TO SEQUENCE LISTING

This specification includes a sequence listing submitted herewith, which includes the file entitled 132463-010124.xml having the following size: 77,937 bytes which was created May 1, 2023, the contents of which are incorporated by reference herein.

TECHNICAL FIELD

The present invention relates generally to fusion proteins that have therapeutic uses, and more specifically to bi-specific fusion proteins, pharmaceutical compositions comprising such fusion proteins, and methods for using such fusion proteins to repair damaged tissue.

BACKGROUND

Myocardial infarction, commonly known as a heart attack, occurs when coronary artery obstruction cuts off the blood supply to part of the heart. The resulting lack of oxygen causes irreversible tissue damage (necrosis and apoptosis), due to the inability of the heart to sufficiently activate endogenous regeneration programs and self-repair. Such tissue damage is a leading cause of congestive heart failure, a condition in which the heart is no longer capable of effectively pumping blood. In the United States, there are more than a million heart attacks every year, and nearly 5 million people are afflicted with congestive heart failure.

There are no effective treatments for regenerating damaged cardiac tissue. Current therapies for congestive heart failure focus on preventing arrhythmia, progression of arteriosclerosis and recurrent myocardial infarction, but do not address the underlying tissue damage. More than half of patients diagnosed with congestive heart failure die within five years of diagnosis.

Stem cell therapy is a potential new strategy for cardiac repair. In the laboratory, it is possible to generate cardiac muscle cells from stem cells. This suggests that stems cells could be used to repair damaged tissue such as cardiac tissue in a patient; however, no therapeutic treatments based on such an approach are presently available. One difficulty that has been encountered in stem cell therapy is that of targeting sufficient numbers of stem cells to the damaged tissue to result in clinically significant repair.

There is, thus, a need in the art for methods for repairing or regenerating damaged tissues, including cardiac tissue, and for improving the targeting of cells such as stem cells to facilitate tissue repair. The present invention fulfills these needs and provides other related advantages.

SUMMARY OF THE INVENTION

The present invention provides bi-specific fusion proteins, nucleic acid molecules encoding bi-specific fusion proteins and therapeutic methods that employ such bi-specific fusion proteins.

In certain aspects, the present invention provides bi-specific fusion proteins that comprise: (a) a targeting domain having a binding specificity to an ischemia-associated molecule; and (b) an activator domain having a binding specificity to a growth factor receptor or cytokine receptor, wherein upon exposure of the activator domain to the growth factor receptor or cytokine receptor, the activator domain binds the growth factor receptor or cytokine receptor so as to modulate regeneration of a cardiac tissue.

In some embodiments, the bi-specific protein comprises: (a) a targeting polypeptide domain that binds to an ischemia-associated molecule with a $K_d$ (i.e., said binding exhibits a $K_d$) ranging from $10^{-6}$ to $10^{-12}$ M or better; and (b) an activator domain that that detectably modulates the activity of a cellular network (e.g., detectably modulates activation of a growth factor receptor or cytokine receptor). In certain embodiments, the targeting polypeptide domain binds to the ischemia-associated molecule with a $K_d$ ranging from $10^{-7}$ to $10^{-12}$ M or better, or ranging from $10^{-8}$ to $10^{-12}$ M or better. In further embodiments, the $K_d$ is determined using a biosensor, e.g., by surface plasmon resonance or resonant mirror analysis.

In addition to components (a) and (b), above, certain bi-specific fusion proteins provided herein further comprise: (c) a polypeptide linker wherein the polypeptide linker extends the half life of the bi-specific fusion protein. In some embodiments, the targeting domain is at the N-terminus or at the C-terminus of the activator domain. In other embodiments, the polypeptide linkers at the N-terminus or at the C-terminus of the targeting domain. In some embodiments, the targeting domain is at the amino terminus of the fusion protein and the activator domain is at the carboxy terminus of the fusion protein. Yet in other embodiments, the targeting domain is at the carboxy terminus of the fusion protein and the activator domain is at the amino terminus of the fusion protein. In some embodiments, the polypeptide linker has two termini, an N-terminus and a C-terminus, that is joined at one terminus via a peptide bond to the targeting polypeptide domain and is joined at the other terminus via a peptide bond to the activator domain. In certain such embodiments, the targeting peptide is linked to the N-terminus of the linker and the activator domain is linked to the C-terminus of the linker. In other such embodiments, the targeting peptide is linked to the C-terminus of the linker and the activator domain is linked to the N-terminus of the linker. In certain embodiments, the linker is non-immunogenic in humans (e.g., a human serum protein or derivative thereof). Representative such linkers comprise at least 100 consecutive amino acids that are at least 80% identical to a serum albumin amino acid sequence, such as a human alpha-fetoprotein sequence. In certain embodiments, the linker comprises or has an amino acid sequence recited in any one of SEQ ID NOs: 10-29.

In some embodiments, the bi-specific fusion protein comprises (a) a targeting domain having a binding specificity to an ischemia-associated molecule; (b) an activator domain that detectably modulates activation of a receptor; and (c) a polypeptide linker, wherein the polypeptide linker extends the half life of the bi-specific fusion protein.

In some embodiments, the bi-specific fusion protein comprises (a) a targeting domain having a binding specificity to a target molecule; (b) an activator domain having a binding specificity to a receptor, wherein upon exposure of the activator domain to the receptor, the activator domain binds the receptor so as to modulate activation of the receptor; and (c) a polypeptide linker, wherein the polypeptide linker extends the half life of the bi-specific fusion protein.

In some embodiments, the bi-specific protein comprises (a) a targeting domain having a binding specificity to a tissue-associated molecule; and (b) an activator domain having a binding specificity to a molecule associated with the surface of a cell in the tissue, wherein upon exposure of the activator domain to surface-associated molecule, the activator domain binds the membrane-associated molecule so as to modulate regeneration of the tissue, wherein the targeting domain and the activator domain are linked via a linker, and wherein the linker extends the half life of the bi-specific fusion protein.

In some embodiments, the bi-specific fusion protein comprises (a) a targeting domain having a binding specificity to a target molecule; (b) an activator domain having a binding specificity to a receptor, wherein upon exposure of the activator domain to the receptor, the activator domain binds the receptor so as to modulate tissue regeneration; and (c) a polypeptide linker, wherein the polypeptide linker extends the half life of the bi-specific fusion protein.

In some embodiments, the targeting domain binds to the molecule with a dissociation constant Kd ranging from $10^{-6}$ M to $10^{-12}$ M. In some embodiments, the targeting domain binds to a molecule selected from the group of myosin, cardiac myosin, DNA, phosphatidylserine, collagen, or extracellular matrix proteins. For example, the targeting domain can be selected from the group of annexin, anti-myosin antibody, anti-DNA scFv, variants thereof, fragments thereof, and combinations thereof. In some embodiments, the scFv antibody has a sequence recited in any one of SEQ ID NOs: 1, 2, or 30. In some embodiments, annexin has a sequence recited in SEQ ID NO: 31.

In some embodiments, the activator domain binds specifically to a growth factor receptor or cytokine receptor. For example, the activator domain is selected from the group consisting of hepatocyte growth factor, vascular endothelial growth factor, fibroblast growth factor, neuregulin/heregulin, variant thereof, and portion thereof.

In other embodiments, the bi-specific fusion proteins comprises (a) a leader polypeptide that comprises a sequence recited in SEQ ID NO:41 or 42; (b) a targeting polypeptide domain that binds to an ischemia-associated molecule, said binding exhibiting a $K_d$ ranging from $10^{-6}$ to $10^{-12}$ M or better; (c) a short connector polypeptide that comprises the sequence -Gly-Ala- or -Ala-Ser-; (d) a HSA polypeptide that comprises a sequence recited in any one of SEQ ID NOs:10, 12, 14-29 and 45); (e) a short connector polypeptide that comprises the sequence -Leu-Gln- or -Thr-Gly-; (f) an activator domain that that detectably modulates the activity of a cellular network; and (g) a hexahistidine-comprising polypeptide.

It will be apparent that the above components may be present in the bi-specific fusion protein in the order recited or in a different order (e.g., the locations of the targeting polypeptide domain and activator domain may be switched). Within certain such bi-specific fusion proteins, the targeting polypeptide domain comprises a sequence recited in SEQ ID NO:1, 2, 30 or 31; the HSA polypeptide comprises the sequence recited in SEQ ID NO:45; the activator domain comprises a sequence recited in any one of SEQ ID NOs: 32-40; and the hexahistidine-comprising polypeptide has a sequence recited in SEQ ID NO:43 or 44.

In certain embodiments of the bi-specific fusion proteins described above, the ischemia-associated molecule is a DNA molecule, myosin (e.g., a myosin subtype such as cardiomyosin) or phosphatidyl serine.

In certain embodiments of the bi-specific fusion proteins described above, the targeting polypeptide comprises an antibody variable region. In certain such embodiments, the targeting polypeptide comprises a scFv antibody. Representative such scFv antibodies comprise or have a sequence recited in SEQ ID NO:1 or SEQ ID NO:2.

In certain embodiments of the bi-specific fusion proteins described above, the activator domain is a growth factor polypeptide. Within certain such embodiments, the growth factor polypeptide binds to a receptor for IGF or HGF (e.g., the growth factor polypeptide comprises or has an amino acid sequence recited in any one of SEQ ID NOs:3-9).

The bi-specific binding agents provided herein are not necessarily limited to two binding specificities. In certain embodiments, in addition to the targeting domain, the bi-specific fusion protein comprises two or more activator domains that are linked directly or indirectly via peptide bonds and are selected from growth factor polypeptides and cytokine polypeptides.

In other aspects, the present invention provides pharmaceutical compositions, comprising a bi-specific fusion protein as described above in combination with a physiologically acceptable carrier.

Within still further aspects, methods are provided for treating pathological tissue damage in a patient, comprising administering a pharmaceutical composition to a patient suffering from pathological tissue damage, and thereby decreasing pathological tissue damage in the patient. In certain embodiments, the pathological tissue damage is heart tissue damage associated with myocardial infarction. In other embodiments, the pathological tissue damage is kidney tissue damage.

In some embodiments, methods are provided for promoting tissue regeneration in a patient. The methods comprise (a) providing a bi-specific fusion protein comprising (i) a targeting domain having a binding specificity to an ischemia-associated molecule; and (ii) an activator domain having a binding specificity to growth factor receptor or cytokine receptor; and (b) administering in a patient in need thereof a therapeutically effective amount of the bi-specific fusion protein whereby the targeting domain specifically binds to the ischemia-associated molecule thereby targeting the bi-specific fusion protein to a tissue and whereby upon exposure of the activator domain to the growth factor receptor or cytokine receptor, the activator domain specifically activates the growth factor receptor or cytokine receptor so as to promote tissue regeneration. In some embodiments, the methods comprise (a) providing a bi-specific fusion protein comprising (i) a targeting domain having a binding specificity to a target molecule; (ii) an activator domain having a binding specificity to a receptor; (iii) a polypeptide linker, wherein the polypeptide linker extends the half life of the bi-specific fusion protein; and (b) administering in a patient in need thereof a therapeutically effective amount of the bi-specific fusion protein whereby the targeting domain specifically binds to the target molecule thereby targeting the bi-specific fusion protein to a first cell and whereby upon exposure of the activator domain to the growth factor receptor, the activator domain specifically activates the receptor of a second cell of a tissue so as to promote tissue regeneration.

In certain embodiments, such methods further comprise the administration of stem cells to the patient. In some embodiments, upon administration of the bi-specific protein, the bi-specific protein prevents cell damage, increases survival, promotes cell growth, promotes motility of stem cells, recruits stem cells, promotes differentiation of stem cells.

Also provided herein are nucleic acid molecules encoding a bi-specific fusion protein as described above. In certain embodiments, the nucleic acid molecule is DNA, and the DNA further comprises transcriptional and translational regulatory sequences operably linked to the bi-specific fusion protein coding sequence, such that transcription and translation of the coding sequence occurs in at least one eukaryotic cell type.

These and other aspects of the present invention will become apparent upon reference to the following detailed description.

DESCRIPTION OF THE SEQUENCE LISTING

SEQ ID NO:1 is the amino acid sequence of the anti-DNA scFv SV-1.

SEQ ID NO:2 is the amino acid sequence of the anti-DNA scFv SV-22.

SEQ ID NO:3 is the amino acid sequence of a growth factor polypeptide corresponding to wild type human IGF-I (mature form).

SEQ ID NO:4 is the amino acid sequence of a growth factor polypeptide corresponding to human IGF-1 with D12A substitution.

SEQ ID NO:5 is the amino acid sequence of a growth factor polypeptide corresponding to human IGF-1 with E9A substitution.

SEQ ID NO:6 is the amino acid sequence of a growth factor polypeptide corresponding to human HGF alpha chain N-K1 domain.

SEQ ID NO:7 is the amino acid sequence of a growth factor polypeptide corresponding to human HGF alpha chain K1 domain.

SEQ ID NO:8 is the amino acid sequence of a growth factor polypeptide corresponding to human HGF alpha chain N-K2 fusion.

SEQ ID NO:9 is the amino acid sequence of a growth factor polypeptide corresponding to human HGF alpha chain K2 domain.

SEQ ID NO:10 is the amino acid sequence of a human serum albumin (HSA) linker with C34S and N503Q substitutions.

SEQ ID NO:11 is the nucleic acid sequence of an HSA linker with C34S and N503Q substitutions.

SEQ ID NO:12 is the amino acid sequence of HSA.

SEQ ID NO:13 is the nucleic acid sequence of HSA.

SEQ ID NO:14 is the amino acid sequence of an HSA linker with C34S and N503Q substitutions and a polypeptide connector.

SEQ ID NO:15 is the amino acid sequence of an HSA linker with C34S and N503Q substitutions and a polypeptide connector.

SEQ ID NO:16 is the amino acid sequence of an HSA linker with C34S and N503Q substitutions and a polypeptide connector.

SEQ ID NO:17 is the amino acid sequence of an HSA linker with C34S and N503Q substitutions and a polypeptide connector.

SEQ ID NO:18 is the amino acid sequence of an HSA linker with C34S and N503Q substitutions and a polypeptide connector.

SEQ ID NO:19 is the amino acid sequence of an HSA linker with a polypeptide connector.

SEQ ID NO:20 is the amino acid sequence of an HSA linker with a polypeptide connector.

SEQ ID NO:21 is the amino acid sequence of an HSA linker with a polypeptide connector.

SEQ ID NO:22 is the amino acid sequence of an HSA linker with a polypeptide connector.

SEQ ID NO:23 is the amino acid sequence of an HSA linker with a polypeptide connector.

SEQ ID NO:24 is the amino acid sequence of an HSA linker with C34S substitution, domain I.

SEQ ID NO:25 is the amino acid sequence of an HSA linker, domain II.

SEQ ID NO:26 is the amino acid sequence of an HSA linker with N503Q substitution, domain III.

SEQ ID NO:27 is the amino acid sequence of an HSA linker, domain I.

SEQ ID NO:28 is the amino acid sequence of an HSA linker, domain II.

SEQ ID NO:29 is the amino acid sequence of human alpha-fetoprotein.

SEQ ID NO:30 is the amino acid sequence of the anti-phosphatidylserine scFv PS4A7.

SEQ ID NO:31 is the amino acid sequence of human annexin V.

SEQ ID NO:32 is an amino acid sequence of a growth factor polypeptide corresponding to human HGF alpha chain N-K1 domain.

SEQ ID NO:33 is an amino acid sequence of a growth factor polypeptide corresponding to human HGF alpha chain K1 domain.

SEQ ID NO:34 is an amino acid sequence of a growth factor polypeptide corresponding to human HGF alpha chain N-K2 domain.

SEQ ID NO:35 is an amino acid sequence of a growth factor polypeptide corresponding to human HGF alpha chain K2 domain.

SEQ ID NO:36 is an amino acid sequence of a growth factor polypeptide corresponding to human VEGF alpha monomer.

SEQ ID NO:37 is an amino acid sequence of a growth factor polypeptide corresponding to human VEGF alpha dimer.

SEQ ID NO:38 is an amino acid sequence of a growth factor polypeptide corresponding to human FGF2.

SEQ ID NO:39 is an amino acid sequence of a growth factor polypeptide corresponding to human NRG1 alpha, EGF-like domain.

SEQ ID NO:40 is an amino acid sequence of a growth factor polypeptide corresponding to human NRG1 alpha, full sequence.

SEQ ID NO:41 is an amino acid sequence of a bi-specific fusion protein leader polypeptide.

SEQ ID NO:42 is an amino acid sequence of a bi-specific fusion protein leader polypeptide.

SEQ ID NO:43 is an amino acid sequence of a C-terminal hexahistidine-comprising polypeptide.

SEQ ID NO:44 is an amino acid sequence of a C-terminal hexahistidine-comprising polypeptide.

SEQ ID NO:45 is an amino acid sequence of a HSA linker.

SEQ ID NO:46 is an amino acid sequence of a HSA linker with N-terminal and C-terminal short connector polypeptides.

SEQ ID NO:47 is an amino acid sequence of a HSA linker with N-terminal and C-terminal short connector polypeptides.

SEQ ID NO:48 is an amino acid sequence of a HSA linker with N-terminal and C-terminal short connector polypeptides.

SEQ ID NO:49 is an amino acid sequence of a HSA linker with N-terminal and C-terminal short connector polypeptides.

DETAILED DESCRIPTION OF THE INVENTION

Figure 1A:
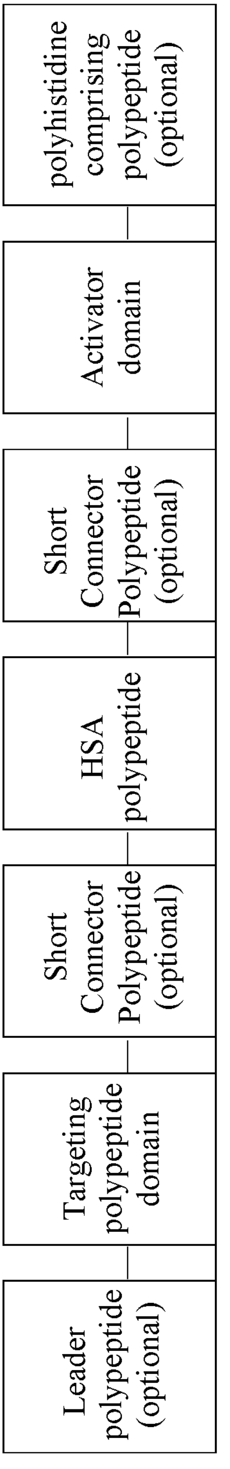
FIGS. 1A and 1B represent different structures of certain bi-specific fusion proteins according to some embodiments.

The present invention is directed to bi-specific fusion proteins that comprise: (1) a targeting polypeptide domain that binds to an ischemia-associated molecule; and (2) an activator domain, such as a growth factor polypeptide or a cytokine polypeptide. In certain embodiments, the bi-specific fusion protein further comprises: (3) a polypeptide linker having two termini, an N-terminus and a C-terminus, that is joined at one terminus via a peptide bond to the targeting polypeptide domain and is joined at the other terminus via a peptide bond to the activator domain. Such bi-specific fusion proteins find use, for example, in recruiting cells that express one or more growth factor and/or cytokine (e.g., chemokine) receptors (e.g., stem cells, progenitor cells or immune system cells) to tissue following an ischemic event (e.g., to damaged cells). In vivo, the administration of such bi-specific fusion proteins may be used to facilitate repair or regeneration of damaged tissue.

The term "polypeptide" is used herein to refer to a molecule that consists of multiple amino acid residues linked by peptide bonds. This term carries no implication as to the number of amino acid residues so linked.

The term "bi-specific" as used herein, refers to the ability of the fusion protein to interact with two different ligands: an ischemia-associated molecule (bound by the targeting polypeptide domain) and a receptor for the activator domain. The binding properties of the targeting polypeptide domain and the activator domain are discussed in more detail below.

An "ischemia-associated molecule" is any molecule that is detected at a level that is significantly higher (e.g., at least 2-fold higher) following ischemia or hypoxia. Any suitable binding assay may be used to identify ischemia-associated molecules, including those provided herein. The increased level of molecule that is detected may be the result of upregulation or decreased turnover, or may be due to increased accessibility (e.g., resulting from cell damage). In certain embodiments, the ischemia-associated molecule is detected in a cell of post-ischemic tissue at a significantly higher level (e.g., at least 2-fold higher) than in a cell of the same tissue that has not undergone an ischemic event (i.e., the molecule is specific to or enriched in the post-ischemic tissue). In further embodiments, the ischemia-associated molecule is associated with cell damage (i.e., the molecule is detected at a significantly higher level in cells that are damaged than in undamaged cells of the same type).

Certain ischemia-associated molecules are enriched (2 fold or higher) in the heart after an ischemic event (or in a model system that is used to mimic ischemia in the heart). Such molecules include, for example, molecules that are exposed on myocytes or other cardiac cells that undergo necrosis (such as DNA) or apoptosis (e.g., phosphatidylserine) or molecules that are enriched in scarred heart tissue, such as collagen (collagen I, III), myosin (including the cell type-specific subtypes thereof), or other extracellular matrix proteins that are enriched in post ischemic hearts. Such molecules can be identified on the basis of enrichment following ischemia-reperfusion in vivo or in simulated ischemia-reperfusion in vitro, or following exposure to conditions such as hypoxia, decreased ATP, increased reactive oxygen species (ROS) or nitric oxide synthase (NOS) production, or serum starvation of cells cultured in vitro.

The Targeting Polypeptide Domain

Binding to the ischemia-associated molecule is mediated by the targeting polypeptide domain. This domain may be any polypeptide sequence that serves this function; in preferred embodiments, the targeting polypeptide domain comprises one or more antibody variable regions.

As used herein, an "antibody" is a protein consisting of one or more polypeptides substantially encoded by immunoglobulin genes. A typical antibody is a tetramer that is composed of two identical pairs of polypeptide chains, each pair having one "light" (about 25 kD) and one "heavy" chain (about 50-70 kD). "$V_L$" and $V_H$" refer to these light and heavy chains respectively. An "antibody variable region" is an N-terminal region of an antibody variable chain ($V_L$ or $V_H$) comprising amino acid residues that are primarily responsible for antigen recognition. Those of ordinary skill in the art are readily able to identify an antibody variable region and to determine the minimum size needed to confer antigen recognition. Typically, an antibody variable region comprises at least 70 amino acid residues, and more commonly at least 100 amino acid residues. A polypeptide that comprises an antibody variable region may (but need not) further comprise other light and/or heavy chain sequences, and may (but need not) further comprise sequences that are not antibody-derived. It will be apparent that the sequence of an antibody variable region may be naturally-occurring, or may be modified using standard techniques, provided that the function (antigen recognition) is retained. Certain polypeptides that comprise an antibody variable region are single chain antibodies (antibodies that exist as a single polypeptide chain), more preferably single chain Fv antibodies (scFv) in which a variable heavy chain region and a variable light chain region are joined together (directly or through a peptide linker) to form a continuous polypeptide. The scFv antibody may be chemically synthesized or may be expressed from a nucleic acid including $V_H$- and $V_L$-encoding sequences either joined directly or joined by a peptide-encoding linker.

"Binding" indicates that an antibody exhibits substantial affinity for a specific antigen (e.g., an ischemia-associated molecule) and is said to occur when the fusion protein (or the targeting polypeptide domain thereof) has a substantial affinity for the target antigen and is selective in that it does not exhibit significant cross-reactivity with other antigens. Preferred substantial binding includes binding with a dissociation constant ($K_d$) of $10^{-6}$, $10^{-7}$, $10^{-8}$, $10^{-9}$, $10^{-10}$, $10^{-11}$, $10^{-12}$ M or better. The $K_d$ of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. $K_d$ is also the ratio of the kinetic on and off rates ($k_{on}$ and $k_{off}$); i.e., $K_d=k_{off}/k_{on}$. Thus, a lower $K_d$ value indicates a higher (stronger) affinity. As used herein, "better" affinities are stronger affinities, and are identified by dissociation constants of lower numeric value than their comparators, with a $K_d$ of $10^{-10}$ M being of lower numeric value and therefore representing a better affinity than a $K_d$ of $10^{-9}$ M. Affinities better (i.e., with a lower $K_d$ value and therefore stronger) than $10^{-7}$ M, preferably better than $10^{-8}$ M, are generally preferred. Values intermediate to those set forth herein are also contemplated, and preferred binding affinity can be indicated as a range of dissociation constants, for example preferred binding affinities for antibodies disclosed herein are represented by $K_d$ values ranging from $10^{-6}$ to $10^{-12}$ M (i.e., micromolar to picomolar), preferably $10^{-7}$ to $10^{-12}$ M, more preferably $10^{-8}$ to $10^{-12}$ M or better. An antibody that "does not exhibit significant cross-reactivity" is one that will not appreciably bind to an off-target antigen. For example, in one embodiment, an antibody that specifically and selectively binds to Annexin V will exhibit at least a two, and preferably three, or four or more orders of magnitude better binding affinity (i.e., binding exhibiting a two, three, or four or more orders of magnitude lower $K_d$ value) for Annexin V than for Annexin molecules other than Annexin V or for non-Annexin proteins or peptides. Binding affinity and selectivity can be determined using any art-recognized methods for determining such characteristics, including, for example, using Scatchard analysis and/or competitive (competition) binding assays.

Binding may be assessed, and $K_d$ values determined, using any of a variety of techniques that are well known in the art. For example, binding to an ischemia-associated DNA molecule is commonly assessed by coating an appropriate solid support (e.g., beads, ELISA plate or BIACORE chip) with target DNA fragments. For a targeting polypeptide domain that binds to any sequence of DNA, DNA fragments (single or double-stranded) of 10 base pairs or larger are immobilized on the solid substrate. For a targeting polypeptide domain that binds to a specific sequence or DNA complex (e.g., DNA-histone complex) the appropriate corresponding target is immobilized. Prior to adding the ischemia-associated molecule, non-specific binding sites for protein are blocked with BSA, milk, or any other appropriate blocker. Uncoated wells or wells coated with a non-target molecule serve as specificity controls. Increasing concentrations of the bi-specific fusion protein (or targeting polypeptide domain) are incubated with target-coated substrate or control substrate. A fusion protein or domain that does not bind to the target is also tested as a specificity control. Target specific, dose-dependent binding of the bi-specific fusion protein (or targeting polypeptide domain) is then assessed by measuring the amount of bi-specific fusion protein (or targeting polypeptide domain) binding to target versus controls as a function of increasing dose using standard protocols corresponding to the solid support and binding technology being used. Representative such protocols include those described in Wassaf et al., *Anal. Biochem.* 351(2):241-53 (2006); Epub 2006 Feb. 10 (BIACORE); and Murray and Brown, *J. Immunol. Methods.* 127(1):25-8 (1990) (ELISA). In addition, studies that vary the amount of immobilized target molecule or that include increasing levels of soluble target molecule as a competitor may also be performed to monitor binding and specificity.

The binding affinity and kinetic on and off rates for binding to the target molecule are measured using standard techniques and compared to other negative control molecules (e.g., fusion protein with irrelevant targeting polypeptide or fusion protein lacking a targeting polypeptide) and positive control molecules (e.g., parental antibody that targets the ischemia-associated molecule, or other antibodies or antibody fragments that are known to bind to the ischemia-associated molecule).

In certain embodiments, the $K_d$ is determined using a biosensor (e.g., by surface Plasmon resonance (BIAcore) or resonant mirror analysis (IAsys)). Such determinations may be performed as described by Hefta et al., Measuring Affinity Using Biosensors, in "Antibody Engineering: A Practical Approach," McCafferty et al. (eds), pp. 99-116 (Oxford University Press, 1996), and references cited therein. Briefly, kinetic on and off rates ($k_{on}$ and $k_{off}$) are determined using a sensor chip to which the ischemia-associated molecule has been coupled. To evaluate association ($k_{on}$), solutions of different concentrations of bi-specific fusion protein (or targeting polypeptide domain) flow across the chip while binding is monitored using mass sensitive detection. Using the BIAcore system (GE Healthcare; Piscataway, NJ), $k_{on}$ is the slope of the plot of dR/dt versus R, where R is the signal observed. Following binding, dissociation is observed by passing a buffer solution across the chip, and $k_{off}$ is determined in an analogous fashion. $K_d$ is then calculated using the equation:

$$K_d = k_{off}/k_{on}$$

In the context of the present invention, a bi-specific fusion protein binds to the ischemia-associated molecule if it binds with a $K_d$ of less than $10^{-8}$ M, preferably less than $10^{-7}$ M, $10^{-8}$ M, $10^{-9}$ M or $10^{-10}$ M. In addition, the binding of the bi-specific fusion protein to the ischemia-associated molecule in this assay is significantly higher (e.g., at least 2-, 10- or 100-fold higher) than binding of the bi-specific fusion protein to negative controls. Preferably, binding to the immobilized target can also be competed using excess soluble target.

As noted above, certain ischemia-associated molecules are specific to (or enriched in) damaged cells. Binding to damaged cells is conveniently demonstrated in vitro using cultured cells that are exposed to conditions that induce necrosis or apoptosis. For example, necrosis can be induced in cultured cardiomyocytes by simulated ischemia/reperfusion, and monitored using a LDH release assay, or trypan blue assay followed by subtraction of the number of cells undergoing apoptosis, essentially as described in Shan et al., *Am. J. Physiol. Cell. Physiol.* 294:833-841 (2008). This assay quantitates the total dead cells and the difference between the total and the number of apoptotic cells is attributed to necrosis, as discussed in more detail below. Conditions that induce apoptosis include exposure to $H_2O_2$, and apoptosis can be monitored using any of a variety of techniques known in the art including, for example, annexin V (SEQ ID No. 31) binding cleavage of target peptide sequences by known caspases that are activated by apoptosis, or DNA laddering (measured by TUNEL assay, essentially as described in Kuramochi, *J. Biol. Chem.* 279(49): 51141-47 (2004)). Binding to the cells undergoing necrosis or apoptosis may be assessed by adding fluorescently labeled bi-specific fusion protein (or targeting polypeptide domain) or appropriate control proteins to cells following the induction of apoptosis or necrosis. After incubation of the proteins with the cells for times ranging from a few minutes to one day, the cells are washed and then the cell-bound fluorescence is measured using immunofluorescence, flow cytometry, or similar techniques. Alternatively, other methods of detecting the bound bi-specific fusion protein (or targeting polypeptide domain) may be used, including radiolabeling or using enzymes conjugated to the bi-specific fusion protein (or targeting polypeptide domain) or to antibodies that bind to the fusion protein (or targeting polypeptide domain), which is common practice in ELISA protocols. The bi-specific fusion protein (or targeting polypeptide domain) binds to target cells if significantly higher (e.g., 2-fold higher) binding to cells following ischemia (e.g., cells undergoing necrosis or apoptosis) is detected, as compared to cells that have not experienced an ischemic event (e.g., cells not undergoing apoptosis or necrosis).

In vivo targeting may be demonstrated by inducing ischemia in an animal model and comparing the level of administered bi-specific fusion protein (or targeting polypeptide domain) in a target tissue before and after ischemia. In vivo targeting to damaged cells may be demonstrated by inducing tissue damage in an animal model, administering the bi-specific fusion protein (or targeting polypeptide domain), and comparing the level of bi-specific fusion protein (or targeting polypeptide domain) in damaged versus undamaged cells. In one embodiment, the bi-specific fusion proteins are designed to target areas of tissue damage following ischemia-reperfusion injury. In such a case, demonstration of in vivo targeting may be accomplished by inducing tissue damage, preferably by a method that causes ischemia followed by re-establishment of blood supply. Numerous methods are available to do this in different tissues. For example, blood flow to the hindlimb of the mouse can be transiently blocked with a simple tourniquet. Alternatively, temporary clamp on the artery leading into the kidney can be employed. Ischemia-reperfusion injury can be induced in the heart through temporary blockage of the coronary artery as demonstrated in mice, rats, dogs, and pigs. Representative methods for inducing tissue damage in an animal model are summarized in Table 1.

TABLE 1

| Representative Methods used to Induce Ischemia-Reperfusion Damage | | |
|---|---|---|
| Organ or tissue | Methods used to induce damage | Reference |
| Heart | Mouse: left anterior descending artery clamped for up to 30 minutes followed by reperfusion | Dumont et al., *Circulation* 102(13): 1564-8 (2000) |
| | Rat: coronary artery ligation | Davis, *Proc. Natl. Acad. Sci. USA* 23: 103(21): 8155-60 (2006) |
| Kidney | Mouse: Renal artery clamped with pediatric suture for 1-6 hrs | Chen et al., *FASEB J.* 4(12): 3033-39 (1990) |
| Liver | Dog: The hepatic pedicle and hepatic artery (close to the celiac artery) were cross-clamped with vascular clamps. | Miranda et al., *Braz. J. Med. Biol. Res.* 40(6): 857-65 (2007) |
| | Pig: Details in reference | Kobayashi et al., *World J. Gastroenterol.* 13(25): 3487-92 (2007) |
| Hindlimb | | Zbinden et al., *Am. J. Physiol. Heart Circ. Physiol.* 292: H1891-H1897 (2007) |

Animal models for ischemia-reperfusion injury are further detailed in the following references:

Greenberg et al., Chapter 7. Mouse models of ischemic angiogenesis and ischemia-reperfusion injury. *Methods Enzymol.* 444:159-74 (2008).

Chimenti et al., Myocardial infarction: animal models. *Methods Mol. Med.* 98:217-26 (2004).

Black S C, In vivo models of myocardial ischemia and reperfusion injury: application to drug discovery and evaluation. *J. Pharmacol. Toxicol. Methods* 43(2):153-67 (2000).

The specificity of targeting can be established by comparing the bi-specific fusion protein (or targeting polypeptide domain) deposition in the clamped versus unclamped kidney as shown in Chen et al., *FASEB J.* 4(12): 3033-39 (1990), or in the treated versus untreated hindlimb as shown in Zbinden et al., *Am. J. Physiol. Heart Circ. Physiol.* 292: H1891-H1897 (2007), using radiolabeled bi-specific fusion protein (or targeting polypeptide domain). Alternatively, bi-specific fusion protein (or targeting polypeptide domain) can be detected in homogenized tissue using ELISA, or can be imaged in real time using bi-specific fusion protein (or targeting polypeptide domain) labeled with the appropriate metal for imaging (e.g., Tc99, Y or Gd). Specific deposition in the damaged area of the heart can be measured as described in Dumont et al., *Circulation* 102(13):1564-8 (2000). Representative methods for demonstrating targeting of proteins to damaged tissue are shown in Table 2.

TABLE 2

| Demonstration of Targeting to Damaged Tissue | | |
|---|---|---|
| Damaged organ or tissue targeted | Methods used to demonstrate targeted delivery | Reference |
| Heart | Humans: Tc99 labeling of Annexin V followed by imaging in humans using SPECT in patients with myocardial infarction followed by reperfusion attempts via angioplasty or thrombolysis | Hofstra et al., *The Lancet* 356 (9225): 209-12 (2000) |
| Heart | Mouse: Fluorescent labeling of Annexin V in murine model of ischemia reperfusion with distribution in the myocardium detected histologically | Dumont et al., *Circulation* 102(13): 1564-8 (2000) |
| Heart | Humans: Tc99 labeling of Annexin V followed by imaging in humans using SPECT in patients undergoing cardiac transplant rejection | Hofstra et al., *The Lancet* 356 (9225): 209-12 (2000) |
| Heart | Mouse: Fluorescently-labeled growth factor imaged in heart tissue using confocal microscopy | Urbanek, *Proc. Natl. Acad. Sci. USA* 102 (24): 8692-97 (2005) |
| Damaged kidney targeted using radiolabeled antibody to DNA | Radiographs of clamped versus unclamped kidney<br>Microautoradiographs to show localization to specific cellular structures in the kidney<br>Imaging of whole mouse using I131-labeled antibody to DNA (versus labeled control)<br>Biodistribution of I125-labeled antibody to show deposition in non-target tissues | Chen et al., *FASEB J.* 4(12): 3033-9 (1990) |

As noted above, certain targeting polypeptide domains comprise a scFv antibody that binds to the ischemia-associated molecule. Representative such scFv antibodies comprise or have the sequences provided herein as SEQ ID NOs: 1, 2, and 30.

It will be apparent that functionally related antibodies may also, or alternatively, be used as a targeting polypeptide domain. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to generate modified antibodies that mimic the properties of an original antibody by combining CDR sequences from one antibody with framework sequences from a different antibody. Such framework sequences can be obtained from public DNA databases that include germline antibody gene sequences.

Thus, one or more CDRs of a targeting polypeptide domain sequence provided herein, can be used to create functionally related antibodies that retain the binding characteristics of the original targeting polypeptide domain. In one embodiment, one or more CDR regions selected from SEQ ID NOs: 1, 2, and 30, is combined recombinantly with known human framework regions and CDRs to create additional, recombinantly-engineered, targeting polypeptide domains. The heavy and light chain variable framework regions can be derived from the same or different antibody sequences. CDR regions are readily identified using alignments with known sequences in databases such as Vbase and IMGT. The resulting targeting polypeptide domains share one or more CDRs with the targeting polypeptide domains of SEQ ID NOs: 1, 2, and 30; in certain embodiments, the targeting polypeptide domain comprises at least one CDR of a sequence as recited in SEQ ID NO: 1, 2, or 30.

It is well known in the art that antibody heavy and light chain CDR3 domains play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 90%, 95%, 98%, 99% or 99.5% identical to the corresponding CDRs of an antibody named herein.

In another embodiment, one or more residues of a CDR may be altered to modify binding to achieve a more favored on-rate of binding. Using this strategy, an antibody having ultra high binding affinity (e.g., $K_d = 10^{-10}$ or less) can be achieved. Affinity maturation techniques, well known in the art, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions of the heavy and/or the light chain variable regions of an antibody, so long as antigen binding affinity subsequent to these modifications is not substantially diminished.

The Activator Domain

The activator domain is any polypeptide that detectably modulates the activity of a cellular network; certain activator domains are growth factor polypeptides or cytokine polypeptides (e.g., a chemokine polypeptide). It will be apparent that such modulation may be an increase or a decrease in the activity of the cellular network. A growth factor polypeptide detectably modulates activation of a growth factor receptor (such as HGF or IGF receptor). Certain such polypeptides are wild-type hepatocyte growth factor (HGF) or HGF alpha chain (e.g., GENBANK accession number P14210), or derivatives thereof that retain at least 10% of wild-type biological activity, as determined by measuring activation of the corresponding growth factor receptor in appropriate target cells. Activation may be assessed, for example, by measuring phosphorylation of receptor kinase or downstream proteins, such as AKT, essentially as described by Nishi et al., *Proc. Natl. Acad. Sci. USA* 95:7018-7023 (1998). MTT and CTG assays known in the art may also be used. Representative growth factor polypeptides have a sequence as recited in SEQ ID NO:3-9 or 32-40, herein. As discussed above for the targeting polypeptide domain, activator domains that share one or more CDRs with the activator domains of SEQ ID NOs: 3-9 or 32-40 are also contemplated; CDRs may be identified and such activator domains may be constructed using well known techniques. Thus, in certain embodiments, the activator domain comprises at least one CDR of a sequence as recited in SEQ ID NO:3-9 or 32-40. Similarly, a cytokine polypeptide modulates activation of the corresponding cytokine receptor, as determined in the same fashion.

In certain embodiments, the activator domain is a growth factor polypeptide, which binds a growth factor receptor on a cell surface. Representative such growth factor receptors are receptors for epidermal growth factor (EGF), Neuregulin/Heregulin (NRG), fibroblast growth factor (FGF), insulin-like growth factor (e.g., IGF-I), platelet-derived growth factor (PDGF), vascular endothelial growth factor (VEGF) and isoforms thereof (e.g., VEGF-A or VEGF-C), teratocarcinoma-derived growth factor 1 (TDGF1), transforming growth factor alpha (TGF-$\alpha$), transforming growth factor beta (TGF-$\beta$) and isoforms thereof (e.g., TGF-$\beta$1 or TGF-$\beta$2), thrombopoietin (THPO) or periostin. Other such receptors include mast/stem cell growth factor receptor (SCFR), hepatocyte growth factor receptor (HGF), ErbB-3, ErbB-4, high affinity nerve growth factor receptor, BDNF/NT-3 growth factors receptor, NT-3 growth factor receptor, or vascular endothelial growth factor receptor 1 (VEGFR-I). Representative cytokine receptors include, for example, FL cytokine receptor, receptor for cytokine receptor common gamma chain, interleukin-10 receptor alpha chain, interleukin-10 receptor beta chain, interleukin-12 receptor beta-1 chain, interleukin-12 receptor beta-2 chain, interleukin-13 receptor alpha-1 chain, interleukin-13 receptor alpha-2 chain, interleukin-17 receptor; interleukin-17B receptor, interleukin 21 receptor precursor, interleukin-1 receptor type I, interleukin-1 receptor type II, interleukin-2 receptor alpha chain, interleukin-2 receptor beta chain, interleukin-3 receptor alpha chain, interleukin-4 receptor alpha chain, interleukin-5 receptor alpha chain, interleukin-6 receptor alpha chain, interleukin-6 receptor beta chain, interleukin-7 receptor alpha chain, high affinity interleukin-8 receptor A, high affinity interleukin-8 receptor B, interleukin-9 receptor, interleukin-18 receptor 1, interleukin-1 receptor-like 1 precursor, interleukin-1 receptor-like 2, toll-like receptor 1, toll-like receptor 2, toll-like receptor 5, CX3C chemokine receptor 1, C-X-C chemokine receptor type 3, C-X-C chemokine receptor type 4, C-X-C chemokine receptor type 5, C-X-C chemokine receptor type 6, C-C chemokine receptor type 1, C-C chemokine receptor type 2, C-C chemokine receptor type 3, C-C chemokine receptor type 4, C-C chemokine receptor type 6, C-C chemokine receptor type 7 precursor, C-C chemokine receptor type 8, C-C chemokine receptor type 9, C-C chemokine receptor type 10, C-C chemokine receptor type 11, chemokine receptor-like 2, and chemokine XC receptor. Still other activator domains are receptors for solute carrier organic anion transporter family, member 1A2 (SLCO1A2), sphingosine kinase 1 (SPHK1), secreted phosphoprotein 1 (SPP1), also called osteopontin (OPN), tumor protein 53 (TP53), troponin T type 1 (TNNT1), TSPY-like protein 2 (TSPYL2), visfatin, WAP four-disulfide core domain 1 (WFDC1), thymosin beta 4, wingless-type MMTV integration site family, member 11 (WNT11). Representative activator domains include, for example, resistin, stromal cell-derived factor-1 (SDF-1), signal-induced proliferation-associated gene 1 (SIPA1), and any of the other ligands listed above, as well as portions and derivatives of the foregoing that substantially retain the ability to bind to cognate receptors.

As an initial test, binding of a bi-specific fusion protein (or activator domain thereof) to the appropriate receptor may be assessed using techniques known in the art. In one representative assay, binding is demonstrated by coating an appropriate solid support with the recombinant ectodomain of the appropriate receptor. An ectodomain from a receptor not recognized by the activator domain of the bi-specific fusion protein is used as a specificity control. A support substrate that does not have any immobilized receptor is also used as a control. Similar to the methods described above for binding to the ischemia-associated molecule, specific, dose-dependent binding to receptor is demonstrated using standard protocols corresponding to the solid support and binding technology being used. In addition, studies that vary the amount of receptor or that include increasing levels of soluble target molecule as a competitor are also performed to monitor binding and specificity. Alternatively, the bi-specific fusion protein is immobilized to a support and the binding of the soluble ectodomain of the corresponding receptor(s) is used to demonstrate dose-dependent, specific binding.

The binding affinity and kinetic on and off rates for binding of the bi-specific fusion protein to the receptor(s) are also measured using standard techniques and compared to other negative control molecules (fusion protein with irrelevant control activator domain, fusion protein lacking an activator domain) and positive control molecules (recombinant wild-type receptor ligand, such as a growth factor or cytokine). The equilibrium and kinetic binding parameters of the bi-specific fusion protein are also compared to the same parameters measured for the un-fused wild-type ligand to determine whether fusion of the ligand to other molecules affects the normal binding of the ligand to its corresponding receptor. Such information may be used to determine the effective dose of the bi-specific fusion protein.

A bi-specific fusion protein binds to immobilized growth factor receptor or cytokine receptor with a significantly higher affinity (e.g., at least 100-fold) than that observed for negative controls. In addition, binding to the immobilized receptor can be competed using excess soluble polypeptide, soluble receptor, or antibodies that bind to polypeptide or receptor and block their interaction. Preferably, the bi-specific fusion protein binds to the growth factor or cytokine receptor with an affinity within 1000-fold of the native ligand binding to its receptor.

A bi-specific fusion protein (and its activator domain) further has the capacity to mediate cognate receptor activation. Such activity may be assessed, for example, using a cellular model of ischemia reperfusion, which uses cultured cardiomyocytes such as neonatal rat ventricular myocytes (NRVM) or cell lines. Simulated ischemia (SI) is generally initiated by metabolic inhibitors (deoxyglucose and dithionite) and metabolites (high potassium, lactate, low pH) or by hypoxia in an anaerobic chamber. Reperfusion is simulated by resuspension in an oxygenated buffer. An in vitro adult cardiomyocyte pellet model of ischemia has been developed that provides the two primary components of ischemia—hypoxia and metabolite accumulation—in the absence of any exogenous metabolic inhibitors or metabolites. Table 3 shows representative methods for demonstrating the ability of a bi-specific fusion protein to prevent damage of cardiomyocytes, promote growth, motility or differentiation of cardiac stem cells and/or promote repair of damaged tissue.

TABLE 3

Activity Assessment Methods

| Aspect | Assay | Reference |
|---|---|---|
| Localization and retention kinetics of activator domain | Detection of activator domain in cell lysate by ELISA<br>Detection of activator domain in cells by immunofluorescence (flow cytometry or microscopic) | Davis, *Proc Natl Acad Sci USA* 103(21): 8155-60 (2006)<br>Urbanek, *Proc. Natl. Acad. Sci. USA* 102 (24): 8692-97 (2005) |
| Signaling by activator domain | Detection of phospho-akt or phosphor-ERK in cells by flow cytometry, immunofluorescence, ELISA, phospho-labeling, or Western | Davis, *Proc Natl Acad Sci USA* 103(21): 8155-60 (2006)<br>Urbanek, *Proc. Natl. Acad. Sci. USA* 102 (24): 8692-97 (2005) |
| Protection of cells against apoptosis following hypoxia or other cell | Annexin V binding by immunofluorescence or flow cytometry<br>Detection of caspase activity<br>TUNEL-assay (reduced number of TUNEL- | |

TABLE 3-continued

| Activity Assessment Methods | | |
|---|---|---|
| Aspect | Assay | Reference |
| stressor | positive cells)<br>DNA laddering<br>Cell viability<br>Enhancement of cardiomyocyte viability following exposure to $H_2O_2$. Number of rod-shaped cells<br>pPCR assessment of gene expression | |
| Protection of cells against necrosis | Reduced necrotic area by H&E staining | |
| Reduction in scar formation | Reduction in number of fibroblastic cells in infarct area<br>Reduction collagen deposition<br>Reduction in other matrix proteins associated with scar formation | |
| Migration of CSC into the infarct area | Time dependent increase in c-kit+, sca-1+, MDR1+ cell numbers and numbers undergoing transition to small myocytes | Urbanek, *Proc. Natl. Acad. Sci. USA* 102 (24): 8692-97 (2005) |
| Myocyte mechanics and cell fusion: | Frequency of distribution of myocyte sizes<br>Peak shortening<br>Velocity of shortening and relengthening<br>Assessment of cell fusion (number of X chromosomes) | Urbanek, *Proc. Natl. Acad. Sci. USA* 102 (24): 8692-97 (2005) |
| Cardiac functional assessment | Comparison of MI-treated versus MI-untreated animals<br>LVEDP<br>LVDP<br>+dp/dT<br>LV Weight<br>Chamber Volume<br>Diastolic Wall Stress<br>Survival | Urbanek, *Proc. Natl. Acad. Sci. USA* 102 (24): 8692-97 (2005) |
| Myocardial regeneration | Composition of regenerated myocardium<br>Assessment of BrdU+ cells in infarct area in treated versus untreated animals<br>Myosin+ cells in the infarct area in treated versus untreated animals | Urbanek, *Proc. Natl. Acad. Sci. USA* 102 (24): 8692-97 (2005) |
| Cardiac structural | Infarct size<br>Fibrosis<br>Cardiomyocyte hypertrophy | Urbanek, *Proc. Natl. Acad. Sci. USA* 102 (24): 8692-97 (2005) |

Native growth factors and cytokines can be used as activator domains. It will be apparent, however, that portions of such native sequences and polypeptides having altered sequences may also be used, provided that such polypeptides retain the ability to activate the cognate receptor (e.g., using one of the assays discussed below, such polypeptides detectably activate the receptor, and preferably activate the receptor to a degree that is at least 1% (preferably at least 10%) of that observed for the native ligand. Certain activator domains that bind to growth factor receptors are provided herein in SEQ ID NOs:3-9 and 32-40. Activity of fusion proteins comprising such sequences is well known in the art (e.g., Hashino et al., *J. Biochem.* 119(4):604-609 (1996); Nishi et al., *Proc. Natl. Acad. Sci. USA* 95:7018-23 (1998)).

An activator domain for a particular application may be selected based on the desired therapeutic outcome. For example, an activator domain that comprises FGF2, VEGF alpha or a portion or derivative thereof that substantially retains the ability to bind to cognate receptor, may generally be used to increase angiogenesis. To increase survival and for stem cell differentiation (regenerative) purposes, activator domains that comprise IGF, HGF or NRG1 (or a portion or derivative thereof) may be used.

In some cases, it may be desirable to assess the activity of both the activator domain and the targeting polypeptide simultaneously. An ELISA may be conveniently used for this purpose.

The substrate of the targeting polypeptide (e.g., DNA) is adsorbed to the ELISA plate, which is then blocked with appropriate BSA containing buffers. The bi-specific fusion protein is then added, followed by addition of recombinant substrate for the activator domain (e.g., if the activator is a growth factor, then the substrate is recombinant cognate receptor or receptor fragment (ectodomain)). This substrate is either fluorescently labeled for detection or detected using a labeled antibody to a region of the receptor that does not significantly affect ligand binding.

The in vivo activity of the bi-specific fusion protein is generally assessed by detecting signaling changes in molecules that are regulated by the activator domain of the bi-specific fusion protein. This typically involves changes in cell surface receptor phosphorylation status or downstream mediators such as phospho-AKT or phospho-ERK as detected by flow cytometry, immunofluorescence, ELISA, phospho-labeling, or Western analysis of treated tissues. Other functional assessments include tests for the number of viable cells by staining and morphological identification, level of apoptosis by Annexin V binding (via immunofluorescence) or flow cytometry, detection of caspase activity, TUNEL-assay (reduced number of TUNEL-positive cells) or DNA laddering. In each case, a bi-specific fusion protein functions in vivo if it induces a significant (e.g., at least 2-fold) change in the level, functional activity or phosphorylation of the regulated molecule detected by the assay.

The repair of damaged tissue in a patient can be assessed using any clinically relevant standard. For example, repair of infracted tissue can be measured by quantitation of cell number, such as the number of myocytes, fibroblast, or amount of scarring, or with functional assays for output or structural aspects of heart function including, LVEDP, LVDP, +dp/dT, LV Weight, Chamber Volume, and Diastolic Wall Stress. Methods for such assessments are well known and amply described in the literature. In general, a bi-specific fusion protein is said to repair damaged tissue if it results in a significant (e.g., at least 2-fold) change in any such clinical assessment.

Polypeptide Linker

The targeting polypeptide domain and activator domain may be directly joined via a peptide bond. Alternatively, they may be joined via a polypeptide linker. It will be apparent that any such linker will have two termini, an N-terminus and a C-terminus. The linker is joined at one terminus via a peptide bond to the targeting polypeptide domain and is joined at the other terminus via a peptide bond to the activator domain. In certain embodiments, the linker is joined at the N-terminus to the C-terminus of the targeting polypeptide domain and at the C-terminus to the N-terminus of the activator domain. In other embodiments, the linker is joined at the C-terminus to the targeting polypeptide domain and at the N-terminus to the activator domain.

Preferably, the linker is non-immunogenic in humans. More preferably, the linker is a human serum protein or a derivative thereof that retains at least 50% sequence identity over a region that consists of at least 100 consecutive amino acids. In further embodiments, the linker comprises at least 100 consecutive amino acids that are at least 70%, 80%, 85%, 90% or 95% identical to a human serum albumin amino acid sequence or a human alpha-fetoprotein amino acid sequence. Representative such linkers include those recited in any one of SEQ ID NOs:10, 12, 14-29 and 45, which may be incorporated into a bi-specific fusion protein alone or using a short (e.g., from 2 to 20 amino acid residues) connector polypeptide at one or both ends. Suitable short connector polypeptides for use at the N-terminal end of the linker include, for example, dipeptides such as -Gly-Ala- (GA) and -Ala-Ser- (AS). Suitable short connector polypeptides for use at the C-terminal end of the linker include, for example, dipeptides such as -Leu-Gln- (LQ) and -Thr-Gly- (TG). SEQ ID NOs:46-49 recite the linker of SEQ ID NO:45 with representative connector dipeptides at both the N- and C-termini; it will be apparent, however, that such short connector polypeptides, if present, may be located at either one or both termini.

Certain preferred linkers provide a prolonged half-life of the bi-specific fusion protein, as compared to fusion protein without linker. The effect of a linker on half-life can be evaluated using an assay that determines stability under physiological conditions. For example, bi-specific fusion protein can be incubated at 37° C. in serum (e.g., human) for 120 hours, with samples removed at the start of incubation and every 24 hours thereafter. Binding assays as described above are then performed to detect the level of functional bi-specific fusion protein at each time point. This level is then compared to the level of bi-specific fusion protein constructed without linker (or using a different linker) to provide a half-life comparison.

Optional Elements and Representative Bi-Specific Fusion Proteins

It will be apparent that elements in addition to those described above may optionally be included in the bi-specific fusion proteins provided herein. Such elements may be present for a variety of purposes, including to facilitate expression, preparation or purification of the bi-specific fusion protein, or to perform targeting functions. For example, an N-terminal leader polypeptide may be present. Representative leader polypeptides comprise or have a sequence recited in SEQ ID NO:41 or 42. A bi-specific fusion protein may also, or alternatively, comprise a polyhistidine (e.g., hexahistidine) tag to facilitate purification. Such a tag comprises at least six histidine consecutive amino acid residues, and may be located at the C- or N-terminus. In certain embodiments, a hexahistidine tag is included at the C-terminus of the bi-specific fusion protein. Additional amino acid residues may also be present at the junction of the polyhistidine to the remainder of the bi-specific fusion protein. Certain bi-specific fusion proteins provided herein comprise a C-terminal polyhistidine-comprising polypeptide as recited in SEQ ID NO:43 or 44.

Figure 1B:
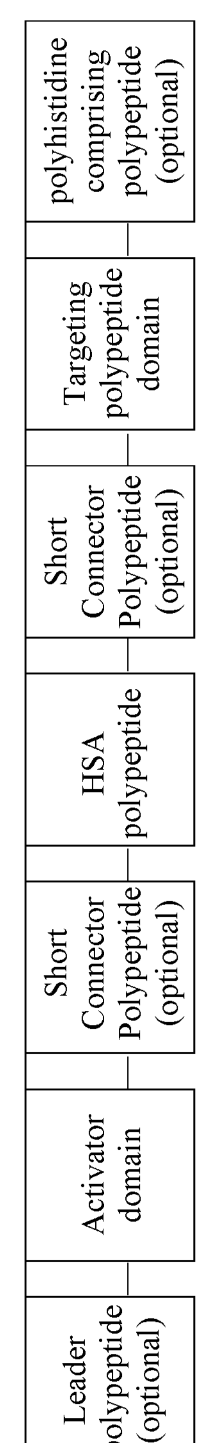

Certain bi-specific fusion proteins have a general structure that satisfies one of the structure shown at FIG. 1A or FIG. 1B (shown from N-terminal to C-terminal, left to right).

Representative bi-specific fusion proteins comprise (from N-terminal to C-terminal):

(a) a leader polypeptide (e.g., comprising or having a sequence recited in SEQ ID NO:41 or 42);

(b) a targeting polypeptide domain (e.g., comprising or having a sequence recited in SEQ ID NO: 1, 2, 30 or 31);

(c) a short connector polypeptide (e.g., comprising or having the sequence Gly-Ala- or -Ala-Ser-);

(d) a HSA polypeptide (e.g., comprising or having a sequence recited in any one of SEQ ID NOs:10, 12, 14-29 and 45);

(e) a short connector polypeptide (e.g., comprising or having the sequence -Leu-Gln- or -Thr-Gly-);

(f) an activator domain (e.g. comprising or having a sequence recited in any one of SEQ ID NOs:3-9 and 32-40); and (g) a polyhistidine-comprising polypeptide (e.g., a hexahistidine-comprising polypeptide, such as a polypeptide comprising or having a sequence recited in SEQ ID NO:43 or 44.

For example, certain such bi-specific fusion proteins comprise (N-terminal to C-terminal): a leader sequence as recited in SEQ ID NO:41 or 42; a targeting polypeptide domain as recited in SEQ ID NO:1, 2, 30 or 31; an HSA polypeptide having the sequence recited in SEQ ID NO:45; a -Gly-Ala or Ala-Ser- connector dipeptide; -Leu-Gln- or -Thr-Gly-; an activator domain having a sequence recited in any one of SEQ ID NOs: 32-40; and a hexahistidine-comprising polypeptide having a sequence recited in SEQ ID NO:43 or 44.

Other bi-specific fusion proteins comprise (from N-terminal to C-terminal):

(a) a leader polypeptide (e.g., comprising or having a sequence recited in SEQ ID NO:41 or 42);

(b) an activator domain (e.g., comprising or having a sequence recited in any one of SEQ ID NOs:3-9 and 32-40);

(c) a short connector polypeptide (e.g., comprising or having the sequence -Gly-Ala- or -Ala-Ser-);

(d) an HSA polypeptide (e.g., comprising or having a sequence recited in any one of SEQ ID NOs:10, 12, 14-29 and 45);

(e) a short connector polypeptide (e.g., comprising or having the sequence -Leu-Gln- or -Thr-Gly-);

(f) a targeting polypeptide domain (e.g., comprising or having a sequence recited in SEQ ID NO: 1, 2, 30 or 31); and (g) a poly-histidine-comprising polypeptide (e.g., comprising or having as sequence recited in SEQ ID NO:43 or 44.

Still further bi-specific fusion proteins comprise (from N-terminal to C-terminal):

(a) a leader polypeptide (e.g., comprising or having a sequence recited in SEQ ID NO:41 or 42);

(b) an activator domain (e.g., comprising or having a sequence recited in any one of SEQ ID NOs:3-9 and 32-40);

(c) an HSA polypeptide that has a sequence recited in any one of SEQ ID NOs:46-49;

(d) a targeting polypeptide domain (e.g., comprising or having a sequence recited in SEQ ID NO: 1, 2, 30 or 31); and (e) a poly-histidine-comprising polypeptide (e.g., comprising or having as sequence recited in SEQ ID NO:43 or 44.

Preparation of Bi-Specific Fusion Proteins

Bi-specific fusion proteins may be synthesized using standard techniques, including liquid- and solid-phase peptide synthesis and recombinant DNA techniques. For solid phase synthesis, the C-terminal amino acid of the sequence is attached to an insoluble support, and the remaining amino acids are added in sequence. For polypeptides longer than about 50 amino acids, shorter regions may be synthesized in this fashion and then condensed to form the longer polypeptide. Methods of forming peptide bonds by activation of a carboxyl terminal end (e.g., by the use of the coupling reagent N, N'-dicyclohexylcarbodiimide) are well known in the art.

For recombinant DNA techniques, DNA encoding the bi-specific fusion protein is prepared chemically or by isolating and ligating DNA encoding each portion of the fusion protein. The DNA coding for each segment of the bi-specific fusion protein may be isolated from known genes or synthesized de novo. Methods for direct chemical synthesis of DNA are well known in the art, and such syntheses are routinely performed using an automated synthesizer. Chemical synthesis produces a single stranded polynucleotide, which is converted into double stranded DNA by hybridization with a complementary sequence or using DNA polymerase. While chemical synthesis of DNA is generally limited to sequences that are shorter than the bi-specific fusion protein, it will be apparent that the full bi-specific fusion protein may be obtained by ligation of shorter sequences in frame. Alternatively, DNA sequences encoding the bi-specific fusion protein are prepared by cloning. Cloning techniques are well known in the art, and are amply described, for example, by standard references such as Sambrook et al., Molecular Cloning: A Laboratory Manual ($3^{rd}$ ed.), Cold Spring Harbor Laboratory Press (2001). Portions of the DNA may be ligated together in frame to generate the full length coding sequence.

Once the DNA encoding the bi-specific fusion protein is obtained, the DNA may be cloned into a vector for expression in a prokaryotic or eukaryotic host cell. Techniques for incorporating DNA into such vectors are well known to those of ordinary skill in the art. Within such an expression vector, the DNA encoding the bi-specific fusion protein is operably linked to the nucleotide sequences necessary for expression (e.g., a suitable promoter and, if necessary, a terminating signal). A promoter is a nucleotide sequence (typically located 5' to the coding sequence) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Preferably, an expression vector further comprises a selectable marker, which confers resistance to a selection. This allows cells to stably integrate the vector into their chromosomes and grow to form foci, which in turn can be cloned and expanded into cell lines. A variety of selectable markers are known in the art, including, for example, genes that provide resistance to ampicillin, methotrexate, mycophenolic acid, the aminoglycoside G-418, hygromycin and puromycin. Those of ordinary skill in the art are knowledgeable in the numerous expression systems available for expression of proteins including *E. coli*, other bacterial hosts, yeast, and various higher eukaryotic cells such as the COS, CHO, HeLa and myeloma cell lines.

Host cells are transformed or transfected with the vector that comprises the DNA encoding the bi-specific fusion protein using standard methods. Expression in the host cell results in transcription of the DNA into the corresponding mRNA, followed by translation of the mRNA to generate the bi-specific fusion protein.

Once expressed, the bi-specific fusion protein can be purified according to standard procedures, including, for example, ammonium sulfate precipitation or affinity column chromatography. Substantially pure compositions of at least about 90 to 95% homogeneity are preferred, and 98 to 99% or more homogeneity is most preferred for pharmaceutical uses. Once purified, partially or to homogeneity as desired, if to be used therapeutically, the polypeptides should be substantially free of endotoxin.

Pharmaceutical Compositions

The present invention also provides pharmaceutical compositions comprising at least one bi-specific fusion protein as described herein, together with at least one physiologically acceptable carrier. Such compositions may be used for treating patients who are suffering from, or at risk for, tissue damage, in order to prevent tissue damage, or to repair or regenerate damaged tissue. Such patients include, for example, patients who have experienced myocardial infarction, kidney damage, and/or ischemic stroke). If desired, other active ingredients may also be included within the pharmaceutical composition, such as stem cells or other agents that facilitate repair of damaged tissue.

As used herein, the term “physiologically acceptable” means approved by a regulatory agency of the Federal or a state government or listed in the U.S. Pharmacopeia or other generally recognized pharmacopeia for use in animals, and more particularly in humans. The term “carrier” refers to a diluent, adjuvant, excipient, or vehicle with which the bi-specific fusion protein is administered. Physiologically acceptable carriers can be sterile liquids, such as water and oils, including those of petroleum, animal, vegetable or synthetic origin (e.g., peanut oil, soybean oil, mineral oil, or sesame oil). Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water and ethanol. The composition, if desired, can also contain minor amounts of wetting or emulsifying agents, or pH buffering agents.

Pharmaceutical compositions may be formulated for any appropriate manner of administration, including, for example, parenteral, intranasal, topical, oral, or local administration, such as by a transdermal means, for prophylactic and/or therapeutic treatment. These compositions can take any of a variety of well known forms that suit the mode of administration, such as solutions, suspensions, emulsions, tablets, pills, capsules, powders, aerosols and sustained-release formulations. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical modes of administration and carriers are described in "Remington: The Science and Practice of Pharmacy," A. R. Gennaro, ed. Lippincott Williams & Wilkins, Philadelphia, PA ($21^{st}$ ed., 2005).

Commonly, the pharmaceutical compositions provided herein are administered parenterally (e.g., by intravenous, intramuscular, or subcutaneous injection), or by oral ingestion or topical application. For parenteral administration, the bi-specific fusion protein can either be suspended or dissolved in the carrier. A sterile aqueous carrier is generally preferred, such as water, buffered water, saline or phosphate-buffered saline. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions. Pharmaceutically acceptable auxiliary substances may also be included to approximate physiological conditions, such as pH adjusting and buffering agents, tonicity adjusting agents, dispersing agents, suspending agents, wetting agents, detergents, preservatives, local anesthetics and buffering agents.

In one preferred embodiment, the pharmaceutical composition is formulated for intravenous administration to a patient (e.g., a human). Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a sealed (e.g., hermetically sealed) container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Compositions intended for oral use may be presented as, for example, tablets, troches, lozenges, aqueous or oily suspensions, dispersible powders or granules, emulsion, hard or soft capsules, or syrups or elixirs. Such compositions may further comprise one or more components such as sweetening agents flavoring agents, coloring agents and preserving agents. Tablets contain the active ingredient in admixture with physiologically acceptable excipients that are suitable for the manufacture of tablets. Such excipients include, for example, inert diluents, granulating and disintegrating agents, binding agents and lubricating agents. Formulations for oral use may also be presented as hard gelatin capsules wherein the active ingredient is mixed with an inert solid diluent, or as soft gelatin capsules wherein the active ingredient is mixed with water or an oil medium. Aqueous suspensions comprise the active materials in admixture with one or more excipients suitable for the manufacture of aqueous suspensions. Such excipients include suspending agents and dispersing or wetting agents. Dispersible powders and granules suitable for preparation of an aqueous suspension by the addition of water provide the active ingredient in admixture with a dispersing or wetting agent, suspending agent and one or more preservatives.

Oily suspensions may be formulated by suspending the active ingredients in a vegetable oil (e.g., arachis oil, olive oil, sesame oil or coconut oil) or in a mineral oil such as liquid paraffin. Pharmaceutical compositions may also be in the form of oil-in-water emulsions. The oily phase may be a vegetable oil or a mineral oil or mixture thereof. Suitable emulsifying agents include, for example, naturally-occurring gums, naturally-occurring phosphatides and anhydrides.

Pharmaceutical compositions may be sterilized by conventional sterilization techniques, or may be sterile filtered. Sterile aqueous solutions may be packaged for use as is, or lyophilized, the lyophilized preparation being combined with a sterile aqueous carrier prior to administration. The pH of an aqueous pharmaceutical composition typically will be between 3 and 11, more preferably between 5 and 9 or between 6 and 8, and most preferably between 7 and 8, such as 7 to 7.5.

Bi-specific fusion proteins provided herein are generally present within a pharmaceutical composition at a concentration such that administration of a single dose to a patient delivers a therapeutically effective amount. A therapeutically effective amount is an amount that results in a discernible patient benefit, such as detectable repair or regeneration of damaged tissue or diminution of symptoms of tissue damage. Therapeutically effective amounts can be approximated from the amounts sufficient to achieve detectable tissue repair or regeneration in one or more animal models exemplified in Table 3. Nonetheless, it will be apparent that a variety of factors will affect the therapeutically effective amount, including the activity of the bi-specific fusion protein employed; the age, body weight, general health, sex and diet of the patient; the time and route of administration; the rate of excretion; any simultaneous treatment, such as a drug combination; and the type and severity of the tissue damage in the patient undergoing treatment. Optimal dosages may be established using routine testing, and procedures that are well known in the art. Dosages generally range from about 0.5 mg to about 400 mg of bi-specific fusion protein per dose (e.g., 10 mg, 50 mg, 100 mg, 200 mg, 300 mg, or 400 mg per dose). In general, compositions providing dosage levels ranging from about 0.1 g to about 100 g per kilogram of body weight per day are preferred. In certain embodiments, dosage unit forms contain between from about 10 g to about 100 g of bi-specific fusion protein.

Pharmaceutical compositions may be packaged for treating or preventing tissue damage (e.g., for treatment of myocardial infarction or kidney damage). Packaged pharmaceutical preparations include a container holding a therapeutically effective amount of at least one pharmaceutical composition as described herein and instructions (e.g., labeling) indicating that the contained composition is to be used for treating tissue damage (such as myocardial infarction or kidney damage) in a patient. Pharmaceutical compositions may be packaged in multiple single dose units, each containing a fixed amount of bi-specific fusion protein in a sealed package. Alternatively, the container may hold multiple doses of the pharmaceutical composition.

Methods of Treatment

The pharmaceutical compositions can be administered to a patient (preferably a mammal such as a cow, pig, horse, chicken, cat, dog, or more preferably a human) to treat pathological tissue damage in the patient. Within the context of the present invention, the term "treatment" encompasses both prophylactic and therapeutic administration. In prophylactic applications, a pharmaceutical composition as described herein is administered to a patient susceptible to or otherwise at risk for developing pathological tissue damage, in order to prevent, delay or reduce the severity of tissue damage. In therapeutic applications, treatment is performed in order to reduce the severity of the pathological tissue damage exist in the patient prior to treatment. Representative pathological tissue damage includes heart tissue damage (e.g., damage associated with myocardial infarction), kidney tissue damage and ischemic stroke.

Any of a variety of known delivery systems can be used to administer a bi-specific fusion protein including, for example, encapsulation in liposomes, microparticles, microcapsules, recombinant cells capable of expressing the bi-specific fusion protein, receptor-mediated, or a retroviral or other nucleic acid vector. The bi-specific fusion protein may be administered by any convenient route, for example by infusion or bolus injection, by absorption through epithelial or mucocutaneous linings (e.g., oral mucosa, rectal and intestinal mucosa, etc.), and may be administered together with other biologically active agents. Administration can be systemic or local. In addition, it may be desirable to introduce the bi-specific fusion protein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the bsBAs of the invention locally to the area in need of treatment; this may be achieved by, for example, local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In another embodiment, a vesicle, such as a liposome, can be used to deliver the bi-specific fusion protein. In yet another embodiment, the bi-specific fusion protein is delivered in a controlled release system; for example, such a controlled release system may be placed at or near the therapeutic target (e.g., an organ of the body that has experienced or is at risk for tissue damage). The use of such delivery systems is well known to those of ordinary skill in the art.

Without wishing to be bound by any particular theory, it is believed that the bi-specific fusion proteins provided herein are effective for treating pathological tissue damage at least in part due to their ability to recruit stem cells to the damaged tissue. In certain cases, sufficient stem cells may reside within the patient (e.g., resident cardiac stem cells). In certain embodiments, however, it may be beneficial to co-administer stem cells (e.g., bone marrow-derived autologous stem cells). Such stem cells may be administered before or after the bi-specific fusion protein, or may be administered simultaneously (either in the same pharmaceutical composition or in separate compositions).

As noted above, the optimal dose depends on certain factors known in the art, but generally ranges from about 0.5 mg to about 400 mg of bi-specific fusion protein per dose (e.g., 10 mg, 50 mg, 100 mg, 200 mg, 300 mg, or 400 mg per dose). A dose of bi-specific fusion protein (within a pharmaceutical composition as described above) can be administered therapeutically to a patient one or more times per hour, day, week, month, or year (e.g., 2, 4, 5, 6, 7, 8, 9, 10, 11, or 12 times per hour, day, week, month, or year). More commonly, a single dose per day or per week comprising an amount of bi-specific fusion protein ranging from about 0.1 g to about 100 g per kilogram of body weight is administered.

In other embodiments, a pharmaceutical composition comprising a bi-specific fusion protein may be administered to a patient in a dosage that ranges from about 0.5 mg per week to about 400 mg per week, about 1.0 mg per week to about 300 mg per week, about 5 mg per week to about 200 mg per week, about 10 mg per week to about 100 mg per week, about 20 mg per week to about 80 mg per week, about 100 mg per week to about 300 mg per week, or about 100 mg per week to about 200 mg per week. Alternatively, a pharmaceutical composition comprising a bi-specific fusion protein may be administered at a dose that ranges from about 0.5 mg every other day to about 100 mg every other day, about 5 mg every other day to about 75 mg every other day, about 10 mg every other day to about 50 mg every other day, or about 20 mg every other day to about 40 mg every other day. A pharmaceutical composition comprising a bi-specific fusion protein may alternatively be administered at a dose that ranges from about 0.5 mg three times per week to about 100 mg three times per week, about 5 mg three times per week to about 75 mg three times per week, about 10 mg three times per week to about 50 mg three times per week, or about 20 mg three times per week to about 40 mg three times per week.

In further embodiments of, a pharmaceutical composition comprising a bi-specific fusion protein is administered to a mammal (e.g., a human) continuously for 1, 2, 3, or 4 hours; 1, 2, 3, or 4 times a day; every other day or every third, fourth, fifth, or sixth day; 1, 2, 3, 4, 5, 6, 7, 8, 9, or 10 times a week; biweekly; 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 times a month; bimonthly; 1, 2, 3, 4, 5, 6, 7, 8, 9, or 10 times every six months; 1, 2, 3, 4, 5, 6, 7, 8, 9, 10, 11, 12, 13, 14, 15, 16, 17, 18, 19, or 20 times a year; or biannually. It will be apparent that a pharmaceutical composition comprising a bi-specific fusion protein may, but need not, be administered at different frequencies during a therapeutic regime.

The following Examples are offered by way of illustration and not by way of limitation. Unless otherwise specified, all reagents and solvents are of standard commercial grade and are used without further purification. Using routine modifications, the procedures provided in the following Examples may be varied by those of ordinary skill in the art to make and use other bi-specific fusion proteins and pharmaceutical compositions within the scope of the present invention.

EXAMPLES

Example I

Preparation of a Representative Bi-Specific Fusion Protein

A bi-specific fusion protein in which targeting polypeptide domain binds to DNA and the activator domain is NRG1 is prepared. The two domains are joined by a modified human serum albumin (HSA) linker. The NRG1 is recombinantly fused to the amino terminus of the HSA linker incorporating a short connector polypeptide and the anti-DNA scFv is recombinantly fused to the carboxy terminus of the modified HSA linker incorporating an additional short connector polypeptide. The modified HSA linker contains two amino acid substitutions. A cysteine residue at position 34 of native HSA is mutated to serine in order to reduce potential protein heterogeneity due to oxidation at this site. An asparagine residue at amino acid 503 of native HSA, which may be sensitive to deamidation, resulting in decreased pharmacologic half-life, is mutated to glutamine. The modified HSA linker confers an extended circulating half-life on the bi-specific fusion protein.

Example II

In Vitro Activity of a Bi-Specific Fusion Protein

The activity of both components of the representative bi-specific fusion protein prepared in Example 1 (in which the targeting polypeptide domain binds to DNA and the activator domain is NRG1) are tested using an ELISA designed to give activity only when both arms of the bi-specific fusion protein are bound to their substrates simultaneously. The ELISA is performed essentially as described in Stokes et al., J. Clin. Pathol. 35(5): 566-573 (1982) and Gripenberg et al., Scand. J. Immunol. 1:151-157 (1978). More specifically, 1 to 50 ng/ml solution of the bi-specific fusion protein in PBS is added to the wells of a plate pre-adsorbed with DNA (Anti-DS-DNA antibody ELISA kit (Alpha Diagnostic International, Dist by AutogenBioclear, UK) and incubated and washed according to manufacturer's directions until the step in which the detection antibody is added. At this stage, 100 μl of 1-50 ng/ml solution of Biotinylated goat anti-human NRG1-ß1 (R&D Systems BAF377) (antibody to the 'activator arm') in PBS/1% BSA/0.05% Tween is added to all wells and incubated for 1 hr at room temperature, washed in PBS with 0.05% Tween-20. 100 μl of Streptavidin-HRP (1:200 dilutions of stock 2 ug/ml, (R&D Systems 890803)) diluted in PBS is added to each well and incubated 30 min at room temperature. After a final wash in PBS with 0.05% Tween-20, 100 μl of SuperSignal ELISA Pico Chemiluminescent Substrate (as per manufacturer's instructions, Pierce, cat#34077) is added and luminescence (representative of positive signal) is measured on Fusion Microplate reader (Packard) or similar instrument.

The amount of signal detected is significantly higher (at least 100-fold higher) in the wells with bi-specific fusion protein than in wells without DNA or negative controls that contain a dead arm (i.e., does not contain an activator domain or targeting polypeptide domain). In addition, the signal is seen to vary with the amount of bi-specific fusion protein added to the wells.

Example III

In Vivo Activity of a Bi-specific Fusion Protein

The in vivo activity of the representative bi-specific fusion protein prepared in Example 1 is determined by detecting signaling changes in a molecule that is regulated by the activator domain of the fusion protein. For the activator domain in this fusion protein NRG1, activity is assessed by detection of increased phosphorylated ErbB-3 in cells of hearts treated with the bi-specific fusion compared to untreated or mock treated hearts. Myocardial infarction is generated in C57BL/6 mice by ligation of the left coronary artery (LCA) following endotracheal intubation, ventilation and thoracotomy. Coronary occlusion is confirmed by acute inspection of color change of the left ventricle wall, and ST elevation on the electrocardiogram before chest closure. Sham-operated mice undergo the same surgical procedure without LCA ligation.

Hearts from normal mice or those following induction of myocardial infarction, from both control and bi-specific fusion protein treated mice, are removed, fixed in 4% paraformaldehyde, embedded, sectioned and mounted as described in Dhein, Mohr and Delmar, Practical Methods in Cardiovascular Research, 2005, p. 473 (Springer, New York). Phospho-ErbB3 antibody (Cell Signaling Technology; Beverly, MA) is used for detection of Phospho-ErbB3 by immunofluorescence. A 2-fold increase or more in phospho-ErbB3 levels in treated versus untreated hearts is observed and is indicative of functional activator. The increase is in either the number (number per field, or percentage of total) of cells exhibiting signal, the intensity of signal per cell, or both.

Example IV

Tissue Damage Repair in Mice Using a Bi-Specific Fusion Protein

A composition comprising the representative bi-specific fusion protein of Example 1 is administered to a mouse following myocardial infarction, induced as described above. Administration is via intravenous injection (e.g., tail vein). Following administration, heart function is assessed as follows. Mice are anesthetized with chloral hydrate (400 mg/kg body weight, i.p.), and the right carotid artery is cannulated with a microtip pressure transducer (model SPR-671, Millar) for the measurements of left ventricular (LV) pressures and LV+ and −dP/dt in the closed-chest preparation. Measurements are compared to those obtained from untreated control mice to confirm that treatment with the bi-specific fusion protein affects heart function. A significant improvement is observed in heart function as assessed using at least one of these measurements.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:

1. A bi-specific fusion protein comprising:

(a) a targeting domain of anti-DNA scFv selected from the group of SEQ ID NOs: 1 and 2; and (b) an activator domain of insulin-like growth factor 1.

2. A pharmaceutical composition comprising a physiologically acceptable carrier and the bi-specific fusion protein of claim 1.

* * * * *